(12) United States Patent
Stevic

(10) Patent No.: US 11,939,284 B2
(45) Date of Patent: Mar. 26, 2024

(54) ACETIC ACID PRODUCTION

(71) Applicant: Twelve Benefit Corporation, Berkeley, CA (US)

(72) Inventor: Luka Stevic, Novi Sad (RS)

(73) Assignee: Twelve Benefit Corporation, Berkeley, CA (US)

( * ) Notice: Subject to any disclaimer, the term of this patent is extended or adjusted under 35 U.S.C. 154(b) by 0 days.

(21) Appl. No.: 18/328,581

(22) Filed: Jun. 2, 2023

(65) Prior Publication Data
US 2024/0051909 A1 Feb. 15, 2024

Related U.S. Application Data

(60) Provisional application No. 63/371,316, filed on Aug. 12, 2022.

(51) Int. Cl.
| C07C 51/12 | (2006.01) |
| C07C 29/151 | (2006.01) |
| C07C 29/78 | (2006.01) |
| C07C 51/43 | (2006.01) |

(52) U.S. Cl.
CPC .......... *C07C 51/12* (2013.01); *C07C 29/1518* (2013.01); *C07C 29/78* (2013.01); *C07C 51/43* (2013.01)

(58) Field of Classification Search
CPC ..... C07C 51/12; C07C 29/1518; C07C 29/78; C07C 51/43
See application file for complete search history.

(56) References Cited

U.S. PATENT DOCUMENTS

| 2,650,245 | A | 8/1953 | Boaden et al. |
| 4,042,496 | A | 8/1977 | Tsushima et al. |
| 4,089,758 | A | 5/1978 | McAloon |
| 4,176,215 | A | 11/1979 | Molnar et al. |
| 4,609,440 | A | 9/1986 | Frese, Jr. et al. |
| 4,828,941 | A | 5/1989 | Sterzel |
| 4,921,586 | A | 5/1990 | Molter |
| 5,039,389 | A | 8/1991 | McMichael |
| 5,601,937 | A | 2/1997 | Isenberg |
| 5,992,008 | A | 11/1999 | Kindler |
| 6,358,651 | B1 | 3/2002 | Chen et al. |
| 7,605,293 | B2 | 10/2009 | Olah et al. |
| 7,608,356 | B2 | 10/2009 | Risen, Jr. et al. |
| 7,704,369 | B2 | 4/2010 | Olah et al. |
| 7,883,817 | B2 | 2/2011 | Hori et al. |
| 8,131,859 | B2 | 3/2012 | Fujii et al. |
| 8,137,859 | B2 | 3/2012 | Shin et al. |
| 8,268,026 | B2 | 9/2012 | Norbeck et al. |
| 8,277,631 | B2 | 10/2012 | Eastman et al. |
| 8,652,104 | B2 | 2/2014 | Goral et al. |
| 8,652,704 | B2 | 2/2014 | Sano et al. |
| 8,658,016 | B2 | 2/2014 | Lakkaraju et al. |
| 8,721,866 | B2 | 5/2014 | Sivasankar et al. |
| 8,845,875 | B2 | 9/2014 | Teamey et al. |
| 8,845,878 | B2 | 9/2014 | Cole et al. |
| 8,956,990 | B2 | 2/2015 | Masel et al. |
| 9,012,345 | B2 | 4/2015 | Masel et al. |
| 9,108,894 | B1 | 8/2015 | Foody et al. |
| 9,145,615 | B2 | 9/2015 | Zhai et al. |
| 9,181,625 | B2 | 11/2015 | Masel et al. |
| 9,193,593 | B2 | 11/2015 | Masel et al. |
| 9,370,773 | B2 | 6/2016 | Masel et al. |
| 9,464,359 | B2 | 10/2016 | Masel et al. |
| 9,481,939 | B2 | 11/2016 | Masel et al. |
| 9,555,367 | B2 | 1/2017 | Masel et al. |
| 9,566,574 | B2 | 2/2017 | Masel et al. |
| 9,580,824 | B2 | 2/2017 | Masel et al. |
| 10,280,378 | B2 | 5/2019 | Masel |
| 10,648,091 | B2 | 5/2020 | Kuhl et al. |
| 10,822,709 | B2 | 11/2020 | Kuhl et al. |
| 10,975,480 | B2 | 4/2021 | Masel |
| 10,975,481 | B2 | 4/2021 | Guo et al. |
| 11,512,403 | B2 | 11/2022 | Kuhl et al. |
| 2003/0059658 | A1 | 3/2003 | Kohler et al. |
| 2005/0239912 | A1 | 10/2005 | Arcella et al. |
| 2006/0016685 | A1 | 1/2006 | Hawkins et al. |
| 2006/0211777 | A1 | 9/2006 | Severinsky |
| 2008/0283411 | A1 | 11/2008 | Eastman et al. |
| 2008/0318093 | A1 | 12/2008 | Lee et al. |
| 2009/0014336 | A1 | 1/2009 | Olah et al. |
| 2009/0117436 | A1 | 5/2009 | Choi et al. |
| 2009/0155102 | A1 | 6/2009 | Park et al. |
| 2010/0137457 | A1 | 6/2010 | Kaplan |

(Continued)

FOREIGN PATENT DOCUMENTS

| CN | 101981744 A | 2/2011 |
| CN | 102308028 A | 1/2012 |

(Continued)

OTHER PUBLICATIONS

Aeshala, L.M. et al., "Effect of solid polymer electrolyte on electrochemical reduction of CO2, Separation and Purification Technology," 94, (2012), pp. 131-137.

AU Office Action dated Sep. 7, 2022, in Application No. AU2019210132.

Badami, M. "Leakage effects on the performance characteristics of a regenerative blower for the hydrogen recirculation of a PEM fuel cell," Energy Conversion and Management, vol. 55, Mar. 2012, pp. 20-25.

Badami, M., "Theoretical model with experimental validation of a regenerative blower for hydrogen recirculation in a PEM fuel cell system," Energy Conversion and Management, vol. 51, Issue 3, Mar. 2010, pp. 553-560.

(Continued)

*Primary Examiner* — Deborah D Carr

(74) *Attorney, Agent, or Firm* — Weaver Austin Villeneuve & Sampson LLP

(57) ABSTRACT

Systems and methods for acetic acid production include synthesizing acetic acid from carbon monoxide produced by a carbon dioxide electrolyzer and hydrogen produced by a water electrolyzer.

20 Claims, 7 Drawing Sheets

(56) References Cited

U.S. PATENT DOCUMENTS

| | | |
|---|---|---|
| 2010/0159347 A1 | 6/2010 | Choi et al. |
| 2010/0324256 A1 | 12/2010 | Ooms et al. |
| 2012/0171583 A1 | 7/2012 | Bocarsly et al. |
| 2012/0328942 A1 | 12/2012 | Thomas-Alyea et al. |
| 2013/0105304 A1 | 5/2013 | Kaczur et al. |
| 2013/0118911 A1 | 5/2013 | Sivasankar et al. |
| 2013/0345325 A1 | 12/2013 | Lecomte et al. |
| 2014/0027303 A1 | 1/2014 | Cole et al. |
| 2014/0034506 A1 | 2/2014 | Teamey et al. |
| 2014/0093799 A1 | 4/2014 | Masel et al. |
| 2014/0151240 A1 | 6/2014 | Bedell et al. |
| 2014/0206894 A1 | 7/2014 | Cole et al. |
| 2014/0206896 A1 | 7/2014 | Sivasankar et al. |
| 2015/0010804 A1 | 1/2015 | Laramie et al. |
| 2015/0030888 A1 | 1/2015 | Popat et al. |
| 2015/0057458 A1 | 2/2015 | Schjodt et al. |
| 2015/0064602 A1 | 3/2015 | Lee et al. |
| 2015/0217266 A1 | 8/2015 | Sherwood |
| 2015/0232999 A1 | 8/2015 | Busskamp et al. |
| 2015/0329979 A1 | 11/2015 | Reytier et al. |
| 2016/0107154 A1 | 4/2016 | Masel et al. |
| 2016/0152905 A1 | 6/2016 | Kelfkens et al. |
| 2016/0161869 A1 | 6/2016 | Avneri et al. |
| 2016/0194766 A1 | 7/2016 | Eastman et al. |
| 2017/0037522 A1 | 2/2017 | Kaczur et al. |
| 2017/0183789 A1 | 6/2017 | Matthews et al. |
| 2017/0218404 A1 | 8/2017 | Simpson et al. |
| 2017/0321333 A1 | 11/2017 | Kuhl et al. |
| 2017/0321334 A1 | 11/2017 | Kuhl et al. |
| 2017/0328239 A1 | 11/2017 | Fleischer et al. |
| 2018/0057950 A1 | 3/2018 | Co et al. |
| 2018/0086984 A1 | 3/2018 | Chen et al. |
| 2018/0086985 A1 | 3/2018 | Von Olshausen et al. |
| 2018/0171495 A1 | 6/2018 | Masel et al. |
| 2018/0194632 A1 | 7/2018 | Jakobsson et al. |
| 2018/0257057 A1 | 9/2018 | Motoshige et al. |
| 2018/0264429 A1 | 9/2018 | Sugano et al. |
| 2018/0265440 A1 | 9/2018 | Kudo et al. |
| 2019/0016594 A1 | 1/2019 | Singh et al. |
| 2019/0032228 A1 | 1/2019 | Krause et al. |
| 2019/0062931 A1 | 2/2019 | Stark et al. |
| 2019/0093241 A1 | 3/2019 | Baldauf et al. |
| 2019/0134570 A1 | 5/2019 | Pintauro et al. |
| 2019/0211463 A1 | 7/2019 | Masel |
| 2019/0226103 A1 | 7/2019 | Kuhl et al. |
| 2019/0233350 A1 | 8/2019 | Sankaranarayanan et al. |
| 2019/0359894 A1 | 11/2019 | Heidel et al. |
| 2020/0095124 A1 | 3/2020 | Rueger |
| 2020/0240023 A1 | 7/2020 | Cave et al. |
| 2020/0308718 A1 | 10/2020 | Patru et al. |
| 2020/0376479 A1 | 12/2020 | Masel |
| 2021/0002775 A1 | 1/2021 | Matsumoto et al. |
| 2021/0047743 A1 | 2/2021 | Goetheer et al. |
| 2021/0164116 A1 | 6/2021 | Kuhl et al. |
| 2021/0381116 A1* | 12/2021 | Kashi ............... C25B 9/77 |
| 2021/0387139 A1 | 12/2021 | Voskian et al. |
| 2022/0136119 A1* | 5/2022 | Flanders ............ C07C 1/0485 |
| | | 435/71.1 |
| 2022/0153656 A1 | 5/2022 | Flanders et al. |
| 2022/0227684 A1 | 7/2022 | Hashimoto |
| 2023/0175088 A1* | 6/2023 | Cintron ............. C25B 11/042 |
| | | 75/471 |
| 2023/0175146 A1* | 6/2023 | Kashi ................ C25B 1/23 |
| | | 204/253 |
| 2023/0202840 A1* | 6/2023 | Flanders ............ B01J 20/10 |
| | | 252/373 |
| 2023/0265572 A1 | 8/2023 | Kuhl et al. |

FOREIGN PATENT DOCUMENTS

| | | |
|---|---|---|
| CN | 102978653 A | 3/2013 |
| CN | 106148992 A | 11/2016 |
| CN | 106463743 A | 2/2017 |
| CN | 109921060 A | 6/2019 |
| CN | 112994054 A | 6/2021 |
| DE | 102007037672 A1 | 2/2009 |
| DE | 102015201132 A1 | 7/2016 |
| DE | 102015214592 A1 | 2/2017 |
| DE | 102016207420 A1 | 10/2017 |
| EP | 3378968 A1 | 9/2018 |
| EP | 3434810 A1 | 1/2019 |
| EP | 3626861 A1 | 3/2020 |
| EP | 3670700 A1 | 6/2020 |
| GB | 1269841 A | 4/1972 |
| JP | H06145379 A | 5/1994 |
| JP | 2009540130 A | 11/2009 |
| JP | 2010526214 A | 7/2010 |
| JP | 2015054994 A | 3/2015 |
| JP | 2015056315 A | 3/2015 |
| JP | 2015513615 A | 5/2015 |
| JP | 2015513616 A | 5/2015 |
| JP | 2016538420 A | 12/2016 |
| JP | 2017048442 A | 3/2017 |
| JP | 2017053013 A | 3/2017 |
| JP | 2017527701 A | 9/2017 |
| JP | 2019205997 A | 12/2019 |
| KR | 100962903 B1 | 6/2010 |
| WO | WO-2007041872 A1 | 4/2007 |
| WO | WO-2007108014 A1 | 9/2007 |
| WO | WO-2008124538 A1 | 10/2008 |
| WO | WO-2011108546 A1 | 9/2011 |
| WO | WO-2012006240 A1 | 1/2012 |
| WO | WO-2013006710 A2 | 1/2013 |
| WO | WO-2013016447 A2 | 1/2013 |
| WO | WO-2014018091 A1 | 1/2014 |
| WO | WO-2014032000 A1 | 2/2014 |
| WO | WO-2014042781 A2 | 3/2014 |
| WO | WO-2014043651 A2 | 3/2014 |
| WO | WO-2014046797 A2 | 3/2014 |
| WO | WO-2014160529 A1 | 10/2014 |
| WO | WO-2015035521 A1 | 3/2015 |
| WO | WO-2015184388 A1 | 12/2015 |
| WO | WO-2016039999 A1 | 3/2016 |
| WO | WO-2017014635 A1 | 1/2017 |
| WO | WO-2017021083 A1 | 2/2017 |
| WO | WO-2017171115 A1 | 10/2017 |
| WO | WO-2018001637 A1 | 1/2018 |
| WO | WO-2018044720 A1 | 3/2018 |
| WO | WO-2019020239 A1 | 1/2019 |
| WO | WO-2019051609 A1 | 3/2019 |
| WO | WO-2019120812 A1 | 6/2019 |
| WO | WO-2019136018 A2 | 7/2019 |
| WO | WO-2019144135 A1 | 7/2019 |
| WO | WO-2020057998 A1 | 3/2020 |
| WO | WO-2020125868 A1 | 6/2020 |
| WO | WO-2020245070 A1 | 12/2020 |
| WO | WO-2021252535 A2 | 12/2021 |
| WO | WO-2022031726 A2 | 2/2022 |

OTHER PUBLICATIONS

Balster, J. et al., "Tailoring the Interface Layer of the Bipolar Membrane", Journal of Membrane Science, vol. 365, No. 1-2, Dec. 2010, pp. 389-398.

Blaszczyk, J., "In-Situ Anode Recirculation Rate Measurement Method (Draft)," Ogura Industrial Corporation, Ballard Power Systems, Full Cell Seminar & Exposition 2011, Oct. 31-Nov. 3, 2011, 22 pages.

BR Office Action dated Nov. 28, 2022, in Application No. BR1120200149381 with English translation.

Casebolt, R., et al., "Effect of Electrolyte Composition and Concentration on Pulsed Potential Electrochemical CO2 Reduction," ChemElectroChem, Chemistry Europe, Accepted Manuscript, 25 pp.

CN Office Action dated Jan. 4, 2023, in CN Application No. CN201980021305.1 with English translation.

Delacourt et al., "Design of an Electrochemical Cell Making Syngas (CO + H2) from CO2 and H2O Reduction at Room Temperature," Journal of The Electrochemical Society, 155 (1), (2008), pp. B42-B49.

(56) References Cited

OTHER PUBLICATIONS

Endrodi, B., "Multilayer Electrolyzer Stack Converts Carbon Dioxide to Gas Products at High Pressure with Multilayer Electrolyzer Stack Converts Carbon," acs Energy Lett. 2019, 4, 1770-1777.
EP search report dated Sep. 14, 2021, in application No. EP19741371. 9.
Ganji P., et al., "Toward Commercial Carbon Dioxide Electrolysis", Advanced Sustainable Systems, Wiley, US, Jun. 9, 2020, vol. 4(8), 22 Pages.
Hori, Y., "Chapter 48: Co2-reduction, catalyzed by metal electrodes," Handbook of Fuel Cells—Fundamentals, Technology and Applications, vol. 2, Electrocatalysis, 2003. pp. 720-733.
IN Office Action dated Feb. 16, 2022, in Application No. IN202037034886.
International Preliminary Report on Patentability dated Feb. 16, 2023 in PCT Application No. PCT/US2021/044378.
International Search Report and Written Opinion dated Apr. 10, 2023 in PCT Application No. PCT/US2022/079335.
International Search Report and Written Opinion dated Apr. 30, 2019, for application No. PCT/US19/014586.
International Search Report and Written Opinion dated Feb. 28, 2022, in Application No. PCT/US2021/044378.
International Search Report and Written Opinion dated Jul. 20, 2023, in Application No. PCT/US2023/017576.
International Search Report and Written Opinion dated Mar. 7, 2023 in PCT Application No. PCT/US2022/081034.
International Search Report and Written Opinion issued in PCT Application No. PCT/US2020/062080 dated Mar. 16, 2021.
James, B.D., et al. 2017 DOE Hydrogen and Fuel Cells Program Review, Fuel Cell Systems Analysis, Strategic Analysis, Project IDI FC163, Jun. 8, 2017, 34 pages.
Jones J H., "The Cativa Process for the Manufacture Plant of Acetic Acid," Platinum Metals, 2000, vol. 44(3), pp. 94-105.
JP Office Action dated Jan. 4, 2023, in Application No. JP2020-561577 with English translation.
JP Office Action dated Jul. 11, 2023 in Application No. JP2023-507462 with English translation.
Kim, C., et al., "Impact of Pulsed Electrochemical Reduction of CO2 on the formation of C2+ Products over Cu," ACS Catal., 2020, 10, 12403-12413.
Kimura, K.W., et al., "Selective Electrochemical CO2 Reduction During Pulsed Potential Stems From Dynamic Interface," ACS Catalysis, ACS Paragon Plus Environment, University of Illinois at Urbana-Champaign, Downloaded from pubs.acs.org on Jun. 30, 2020, 31 pages.
Kriescher, Stefanie M.A. et al., "A membrane electrode assembly for the electrochemical synthesis of hydrocarbons from C02(g) and Ho2(g), Electrochemistry Communications," 50 (2015), pp. 64-68.
Li, et al., "Electrolysis of Co2 to Syngas in Bipolar Membrane-Based Electrochemical Cells," ACS Publications, ACS Energy Letters, 2016, 1, pp. 1149-1153.
Li, et al., "Electrolytic Conversion of Bicarbonate into CO in a Flow Cell," Cell Press, Joule 3, Jun. 19, 2019, pp. 1487-1497.
Liew, F. et al., "Gas Fermentation-A Flexible Platform for Commercial Scale Production of Low-Carbon-Fuels and Chemicals from Waste and Renewable Feedstocks", Frontiers in Microbiology, May 11, 2016, vol. 7, No. 694, pp. 1-28.

Office Action dated Apr. 1, 2021, in U.S. Appl. No. 16/254,255.
Qi J et al., "Selective Methanol Carbonylation to Acetic Acid on Heterogeneous Atomically Dispersed ReO4/SiO2 Catalysts," Journal of the American Chemical Society, 2020, vol. 142(33), pp. 14178-14189.
Sharma, et al., "Electrocatalytic conversion of carbon dioxide to fuels: a review on the interaction between CO2 and the liquid electrolyte," WIREs Energy Environ 2017, 6:e239. doi: 10.1002/wene.239, pp. 1-21.
Shi, L. et al., "A shorted membrane electrochemical cell powered by hydrogen to remove CO2 from the air feed of hydroxide exchange membrane fuel cells", Nature Energy, Mar. 2022, vol. 7, 36 pages.
Spets et al. "Direct Glucose Fuel Cell With Anion Exchange Membrane in the Near Neutral State Electrolyte, International Journal of Electrochemical Science," 7, 11696-11705, Dec. 1, 2012, entire document, http.electrochemsci.org/papers/vol?/71211696.pdf.
Srinivasan, S. et al., "Advances in Solid Polymer Electrolyte Fuel Cell Technology with Low Platinum Loading Electrodes," Journal of Power Sources, 22 (1988) pp. 359-375.
U.S. Notice of Allowance dated Sep. 1, 2022 in U.S. Appl. No. 16/254,255.
U.S. Final office Action dated Aug. 21, 2023 in U.S. Appl. No. 17/452,395.
U.S. Non-Final office Action dated Jan. 20, 2023 in U.S. Appl. No. 17/452,395.
U.S. Non-Final Office Action dated Oct. 22, 2021, in U.S. Appl. No. 16/254,255.
U.S. Appl. No. 18/051,944, inventors Kuhl et al., filed Nov. 2, 2022.
U.S. Appl. No. 18/295,412, inventors Flanders et al., filed Apr. 4, 2023.
U.S. Appl. No. 18/324,929, inventors Huo Ziyang et al., filed May 26, 2023.
U.S. Restriction Requirement dated Dec. 15, 2022 in U.S. Appl. No. 17/452,395.
U.S. Restriction requirement dated Jun. 23, 2023, in U.S. Appl. No. 17/444,356.
Verma, et al., "The effect of electrolyte composition on the electroreduction of CO2 to CO on Ag based gas diffusion electrodes," Phys. Chem. Chem. Phys., 2016, 18, pp. 7075-7084.
Voskian, S. et al., "Faradaic electro-swing reactive adsorption for CO2 capture", Energy & Environmental Science, 2019, vol. 12, pp. 3530-3547.
Xia, Chuan, et al., "Continuous production of pure liquid fuel solutions via electrocatalytic CO2 reduction using solid electrolyte devices," Nature Energy, http://www.nature.com/natureenergy; https://doi.org/10.1038/s41560-019-0451-x.
Xu, Y., et al., "Self-Cleaning CO2 Reduction Systems: Unsteady Electrochemical Forcing Enables Stability," ACS Energy Letters, 2021, 6, pp. 809-815.
Zhu, Wenlei et al., "Monodisperse Au Nanoparticles for Selective Electrocatalytic Reduction of CO2 to CO.Journal of the American Chemical Society," 2013, 135, p. 16833-16836.
Kalck, P., et al., "Recent Advances in the Methanol Carbonylation Reaction Into Acetic Acid," Coordination Chemistry Reviews, 2020, vol. 402, 58 pages.
European Office Action dated Sep. 4, 2023 in Application No. EP19741371.9.
International Search Report and Written Opinion dated Sep. 21, 2023, in Application No. PCT/US2023/024371.
SA Office Action dated Sep. 26, 2023, in application No. SA522441684 with English Translation.
U.S. Non-Final Office Action dated Oct. 5, 2023, in U.S. Appl. No. 17/444,356.

\* cited by examiner

ACETIC ACID PRODUCTION

INCORPORATION BY REFERENCE

An Application Data Sheet is filed concurrently with this specification as part of the present application. Each application that the present application claims benefit of or priority to as identified in the concurrently filed Application Data Sheet is incorporated by reference herein in their entireties and for all purposes.

TECHNICAL FIELD

This disclosure relates generally to acetic acid production, and more specifically to a new and useful system and method for advantageously reacting carbon dioxide electrolyzer products to form acetic acid.

BACKGROUND

Since carbon dioxide is considered to be a cause of deleterious climate change, new and more robust methods to sequester carbon dioxide ($CO_2$) and/or efficiently convert it to useful products are still highly desirable in the quest to protect the environment while safeguarding valuable and limited resources.

The background description provided herein is for the purposes of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

SUMMARY

Systems and methods for acetic acid production include synthesizing acetic acid from carbon monoxide produced by a carbon dioxide electrolyzer and hydrogen produced by a water electrolyzer.

One aspect of the disclosure relates to a system for producing acetic acid from carbon dioxide including:
(a) one or more carbon dioxide reduction electrolyzers, each including a cathode catalyst for facilitating chemical reduction of carbon dioxide to carbon monoxide;
(b) a water electrolyzer including a cathode catalyst for facilitating chemical reduction of water to hydrogen;
(c) a methanol synthesis reactor configured to receive carbon monoxide produced by the one or more carbon dioxide reduction electrolyzers and hydrogen produced by the water electrolyzer and configured to produce methanol; and
(d) an acetic acid synthesis reactor configured to receive methanol produced by the methanol synthesis reactor and carbon monoxide produced by the one or more carbon dioxide reduction electrolyzers and configured to produce acetic acid.

In some embodiments, the system further includes a heat integration loop configured to receive heat produced by exothermic reactions in the methanol synthesis reactor and the acetic acid synthesis reactor and heat feed streams to the methanol synthesis reactor and the acetic acid synthesis reactor. In some embodiments, the received heat converts boiling water to saturated steam and heating the feed streams converts the saturated steam to boiling water. In some embodiments, the heat integration loop includes a first heat exchanger configured to heat a first feed stream including carbon monoxide and hydrogen to a first elevated temperature. In some embodiments, the system further includes a first auxiliary heater configured to heat the first feed stream from the first elevated temperature to a methanol synthesis reaction temperature. In some embodiments, the heat integration loop includes a second heat exchanger configured to heat a second feed stream including carbon monoxide and methanol to a second elevated temperature. In some embodiments, the boiling water and saturated steam in the heat integration loop are at constant temperature. In some embodiments, the system further includes a second auxiliary heater configured to heat the second feed stream including carbon monoxide and methanol from the second elevated temperature to an acetic acid synthesis reaction temperature. In some embodiments, the system includes multiple carbon dioxide electrolyzers and/or water electrolyzers.

In some embodiments, the methanol synthesis reactor is configured to output a first output stream including methanol, carbon monoxide, and hydrogen. In some embodiments, the system further includes a cooler configured to cool the first output stream to a first reduced temperature. In some embodiments, the system further includes a condenser configured to condense the methanol produced in the methanol synthesis reactor. In some embodiments, the system further includes a recycle path for recycling the hydrogen and carbon monoxide in the first output stream from the first output stream to a feed stream to the methanol synthesis reactor.

In some embodiments, the acetic acid synthesis reactor is configured to output a second output stream including acetic acid, methanol, and carbon monoxide. In some embodiments, the system further includes a junction configured to split an output of the one ore carbon dioxide reduction electrolyzers including carbon monoxide to a first carbon monoxide stream and a second carbon monoxide stream. In some embodiments, the first carbon monoxide stream is input to the methanol synthesis reactor and the second carbon monoxide stream is input into the acetic acid synthesis reactor. In some embodiments, the system further includes one or more distillation columns for separating acetic acid from methanol to produce an acetic acid product stream. In some embodiments, the system further includes a recycle path for recycling methanol to the acetic acid synthesis reactor. In some embodiments, the recycle path includes a distillation column for separating acetic acid from methanol.

In some embodiments, an output of the methanol synthesis reactor includes methanol, carbon monoxide, and hydrogen. In some embodiments, the system includes a first condenser configured to separate the methanol from the carbon monoxide and the hydrogen. In some embodiments, a condensed output of the first condenser includes methanol and water. In some embodiments, the system further includes a water absorber unit configured to remove water from the methanol. In some embodiments, the water is produced as a byproduct in the methanol synthesis reactor.

In some embodiments, an output of the one or more carbon dioxide reduction electrolyzers includes carbon dioxide. In some embodiments, the system further includes a recycle path to recycle the separated carbon monoxide and hydrogen. In some embodiments, the recycle path includes a recirculation compressor.

In some embodiments, an output of the acetic acid synthesis reactor includes acetic acid, methanol, and carbon monoxide. In some embodiments, the system further includes a second condenser configured to separate the acetic acid and methanol from the carbon monoxide. In some embodiments, the system further includes a recycle path configured to recycle the separated carbon monoxide to the acetic acid synthesis reactor.

In some embodiments, the system further includes a junction mixing carbon monoxide produced by the one or more carbon dioxide reduction electrolyzers and hydrogen produced by the water electrolyzer to form a methanol synthesis reactor feed stream.

In some embodiments, the system further includes one or more compressors configured to compress the methanol synthesis reactor feed stream to a first reaction pressure.

In some embodiments, the system further includes a junction mixing a compressed carbon monoxide and hydrogen recycle stream with the compressed methanol synthesis reactor feed stream.

In some embodiments, an operating pressure of the methanol synthesis reactor is at least twice that of an operating pressure of the acetic acid synthesis reactor.

Another aspect of the disclosure relates to a method for producing acetic acid including:
receiving carbon monoxide produced by one or more carbon dioxide reduction electrolyzers and hydrogen produced by a water electrolyzer;
directing a first feed stream including carbon monoxide from the one or more carbon dioxide reduction electrolyzer from the and hydrogen from the water electrolyzer to a methanol synthesis reactor;
synthesizing methanol in the methanol synthesis reactor;
directing a second feed stream including methanol from the methanol synthesis reactor and carbon monoxide from the one or more carbon dioxide reduction electrolyzers to an acetic acid synthesis reactor; and synthesizing acetic acid in the acetic acid synthesis reactor.

In some embodiments, the method further includes circulating boiling water and saturated steam in a heat integration loop configured to receive heat produced by exothermic reactions in the methanol synthesis reactor and the acetic acid synthesis reactor and heat the first and second feed streams. In some embodiments, the received heat converts boiling water to saturated steam and heating the first and second feed streams converts the saturated steam to boiling water. In some embodiments, the heat integration loop includes a first heat exchanger and further including heating the first feed stream including carbon monoxide and hydrogen to a first elevated temperature in the first heat exchanger. In some embodiments, the method further includes heating the first feed stream from the first elevated temperature to a methanol synthesis reaction temperature. In some embodiments, the heat integration loop includes a second heat exchanger and further including heating the second feed stream including carbon monoxide and methanol to a second elevated temperature in the second heat exchanger. In some embodiments, the method further includes heating the second feed stream including carbon monoxide and methanol from the second elevated temperature to an acetic acid synthesis reaction temperature. In some embodiments, the method further includes maintaining the boiling water and saturated steam in the heat integration loop at constant temperature.

In some embodiments, the method further includes outputting a first output stream including methanol, carbon monoxide, and hydrogen from the methanol synthesis reactor. In some embodiments, the method further includes cooling the first output stream to a first reduced temperature. In some embodiments, the method further includes condensing the methanol produced in the methanol synthesis reactor. In some embodiments, the method further includes recycling the hydrogen and carbon monoxide in the first output stream from the first output stream to the first feed stream.

In some embodiments, the method further includes outputting a second output stream including acetic acid, methanol, and carbon monoxide from the acetic acid synthesis reactor.

In some embodiments, the method further includes splitting an output of the one or more carbon dioxide reduction electrolyzers including carbon monoxide to a first carbon monoxide stream and a second carbon monoxide stream.

In some embodiments, the method further includes inputting the first carbon monoxide stream to the methanol synthesis reactor and inputting the second carbon monoxide stream to the acetic acid synthesis reactor.

In some embodiments, the method further includes separating acetic acid from methanol to produce an acetic acid product stream. In some embodiments, the method further includes recycling methanol to the acetic acid synthesis reactor. In some embodiments, recycling methanol includes separating acetic acid from methanol in a distillation column.

In some embodiments, an output of the methanol synthesis reactor includes methanol, carbon monoxide, and hydrogen. In some embodiments, the method further includes separating the methanol from the carbon monoxide and the hydrogen in a first condenser. In some embodiments, a condensed output of the first condenser includes methanol and water. In some embodiments, the method further includes removing water from the methanol. In some embodiments, the water is produced as a byproduct in the methanol synthesis reactor.

In some embodiments, receiving carbon monoxide includes receiving carbon monoxide mixed with carbon dioxide.

In some embodiments, the method further includes recycling the separated carbon monoxide and hydrogen.

In some embodiments, the method further includes repressurizing the recycled carbon monoxide and hydrogen.

In some embodiments, an output of the acetic acid synthesis reactor includes acetic acid, methanol, and carbon monoxide. In some embodiments, the method further includes separating the acetic acid and methanol from the carbon monoxide in a second condenser. In some embodiments, the method further includes recycling the separated carbon monoxide to the acetic acid synthesis reactor.

In some embodiments, the method further includes mixing carbon monoxide produced by the one or carbon dioxide reduction electrolyzers and hydrogen produced by the water electrolyzer to form a methanol synthesis reactor feed stream.

In some embodiments, the method further includes compressing the methanol synthesis reactor feed stream to a first reaction pressure. In some embodiments, the method further includes mixing a compressed carbon monoxide and hydrogen recycle stream with the compressed methanol synthesis reactor feed stream to form the first feed stream. In some embodiments, an operating pressure of the methanol synthesis reactor is at least twice that of an operating pressure of the acetic acid synthesis reactor.

These and other features of the disclosure will be described in detail below with reference to associated figures.

DETAILED DESCRIPTION

Definitions

Figure 1:
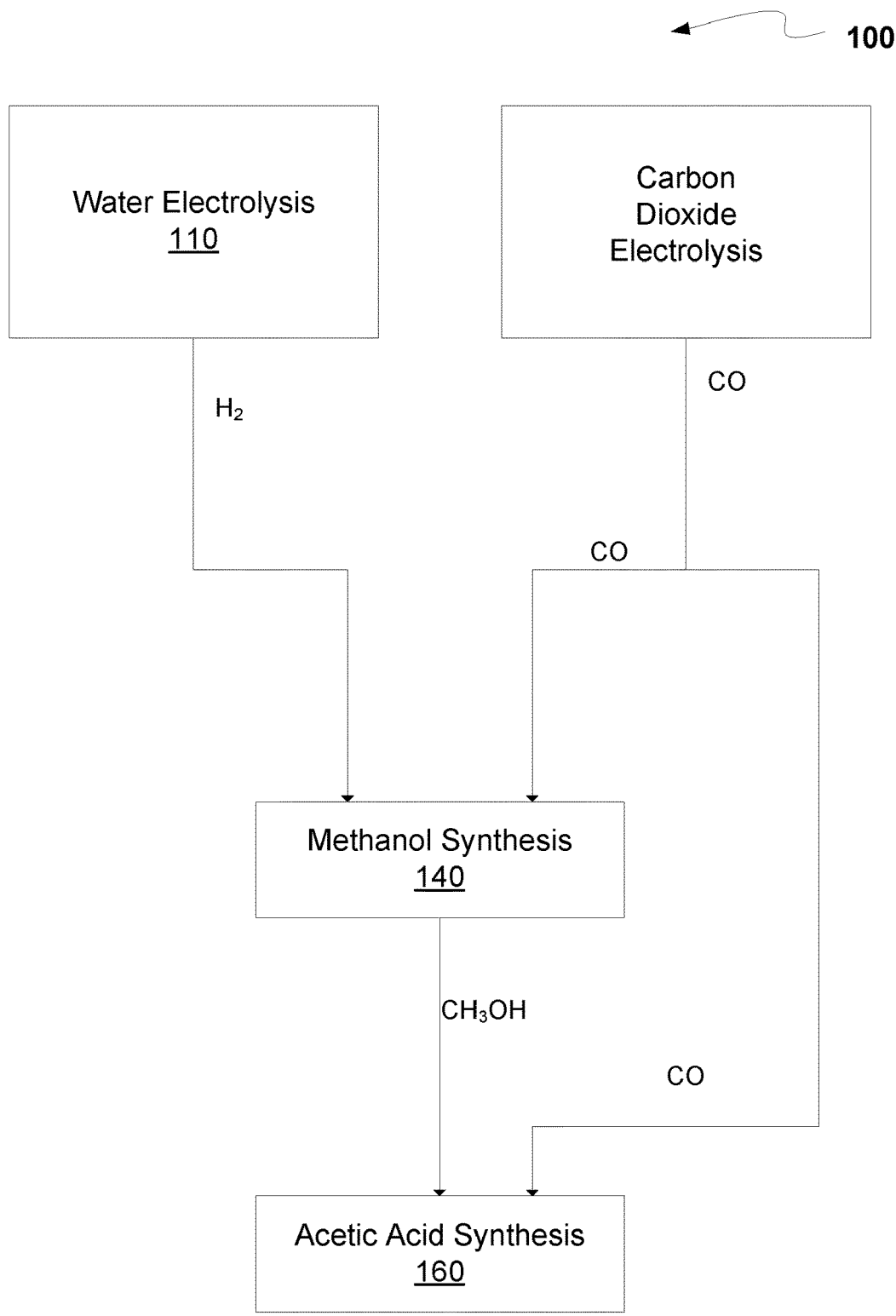
FIG. 1 is a flow chart representation of an embodiment of a method disclosed herein, illustrating acetic acid synthesis from carbon monoxide (CO) supplied from a carbon dioxide ($CO_2$) electrolyzer and hydrogen ($H_2$) supplied from a water electrolyzer.

As used herein, the term "about" is understood to account for minor increases and/or decreases beyond a recited value, which changes do not significantly impact the desired function the parameter beyond the recited value(s). In some cases, "about" encompasses +/−10% of any recited value. As used herein, this term modifies any recited value, range of values, or endpoints of one or more ranges.

As used herein, the phrase "recycle path" means any combination of condensation, purification, and separation units necessary to prepare a reaction intermediate, byproduct, carrier gas or solvent for reuse, including means (e.g. delivery lines, compressors, pumps, or the like) to return the recovered intermediate, byproduct, solvent and/or carrier gas to a reactor or other suitable re-entry point in the production process.

In the following description, numerous specific details are set forth to provide a thorough understanding of the presented embodiments. The disclosed embodiments may be practiced without some or all of these specific details. In other instances, well-known process operations have not been described in detail to not unnecessarily obscure the disclosed embodiments. While the disclosed embodiments will be described in conjunction with the specific embodiments, it will be understood that it is not intended to limit the disclosed embodiments.

Acetic Acid Synthesis from Carbon Monoxide and Hydrogen

Aspects of this disclosure pertain to systems and methods that integrate electrolyzers with methanol and acetic acid synthesis reactors. Acetic acid ($CH_3COOH$) can be produced from carbon monoxide (CO) and hydrogen ($H_2$) feeds with methanol ($CH_3OH$) as an intermediate product. As explained elsewhere herein, a carbon dioxide reduction electrolyzer can be configured to efficiently reduce carbon dioxide ($CO_2$) to carbon monoxide. A water electrolyzer can efficiently decompose ($H_2O$) to form $H_2$ gas.

In certain embodiments, acetic acid is produced using only CO and $H_2$ as feed materials. Carbon monoxide produced by a carbon dioxide electrolyzer, and hydrogen produced by a water electrolyzer are reacted to form methanol. Carbon monoxide produced by a carbon dioxide electrolyzer is reacted with the methanol to form acetic acid.

The methanol synthesis reaction may be given by the following chemical equation:

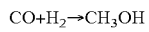

The acetic acid synthesis reaction may be given by the following chemical equation:

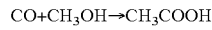

Both reactions may take place at elevated temperatures and are exothermic. In certain embodiments, a heat integration loop is used to recover the heat generated in the reactors and heat the reactor feed streams.

Examples of aspects of the systems and methods are described with respect to FIGS. 1-3, with a detailed example of a system according to certain embodiments described below with respect to FIGS. 4A and 4B. A $CO_2$ membrane electrode assembly and electrolyzer system to produce carbon monoxide are described further below with respect to FIGS. 5 and 6.

FIG. 1 is a schematic flow chart of certain embodiments; illustrating an operation 100, wherein a hydrogen product gas from water electrolysis 110 and a carbon monoxide product gas from a carbon dioxide electrolysis 120 are used in methanol synthesis 140. Carbon monoxide from carbon dioxide electrolysis 120 and methanol produced by methanol synthesis 140 are used as reactants in the acetic acid synthesis 160. As shown, the carbon monoxide generated in the carbon dioxide electrolyzer 120 is split evenly to form feed streams for the methanol synthesis 140 and acetic acid synthesis 160. According to various embodiments, any number of water electrolyzers and carbon dioxide electrolyzers may be employed, with the product streams directed as appropriate to supply the reactant feed streams for each reaction.

In the example of FIG. 1, the hydrogen product gas is produced by water electrolysis, however, other sources of hydrogen gas may be used instead of or in addition to water electrolysis. In some embodiments, excess hydrogen is output from the $CO_2$ electrolyzer along with carbon monoxide and is a portion of the hydrogen used in methanol synthesis.

Figure 2:
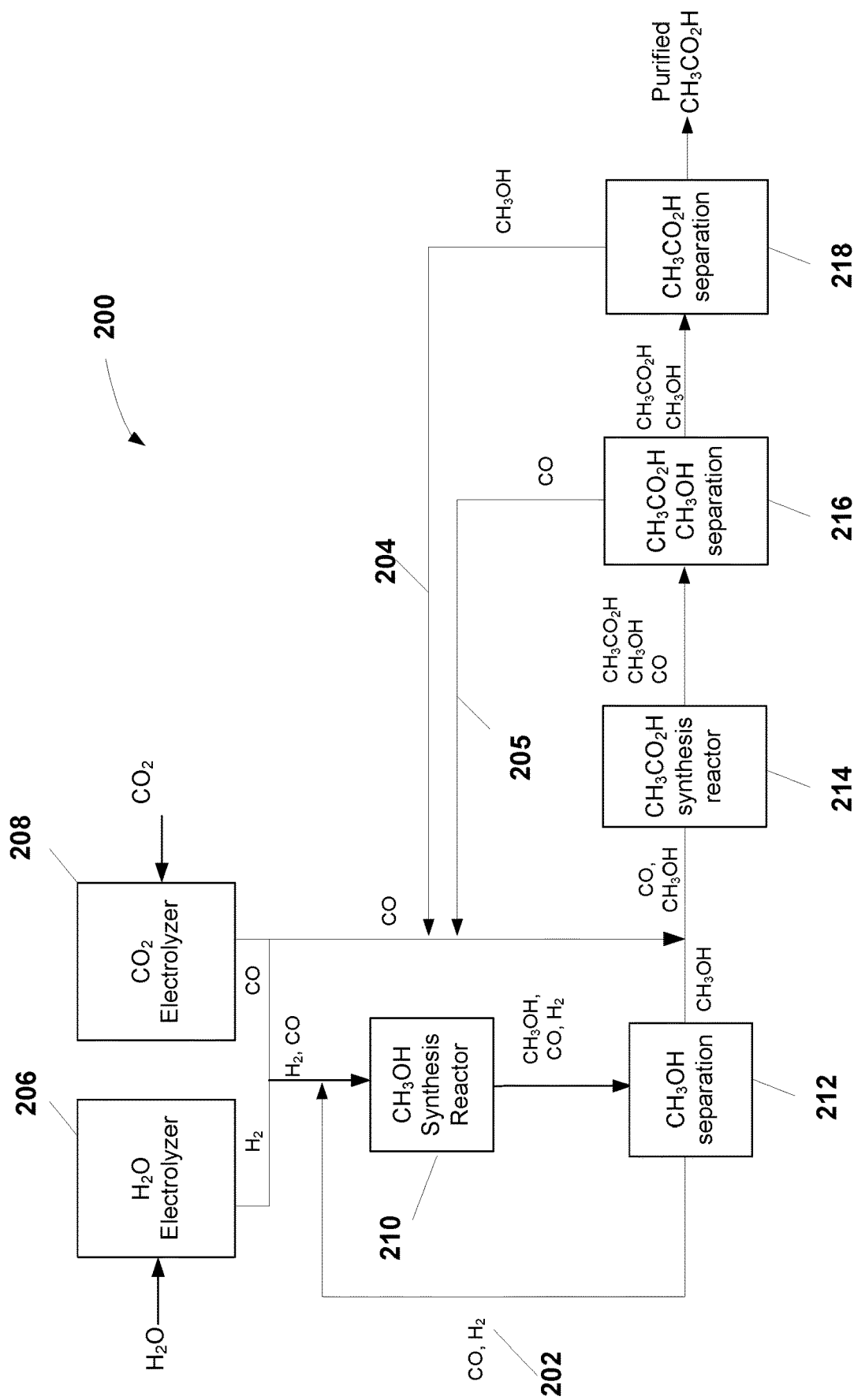
FIG. 2 is a schematic flow chart of certain embodiments of a system for producing acetic acid including three recycle paths.
Figure 3:
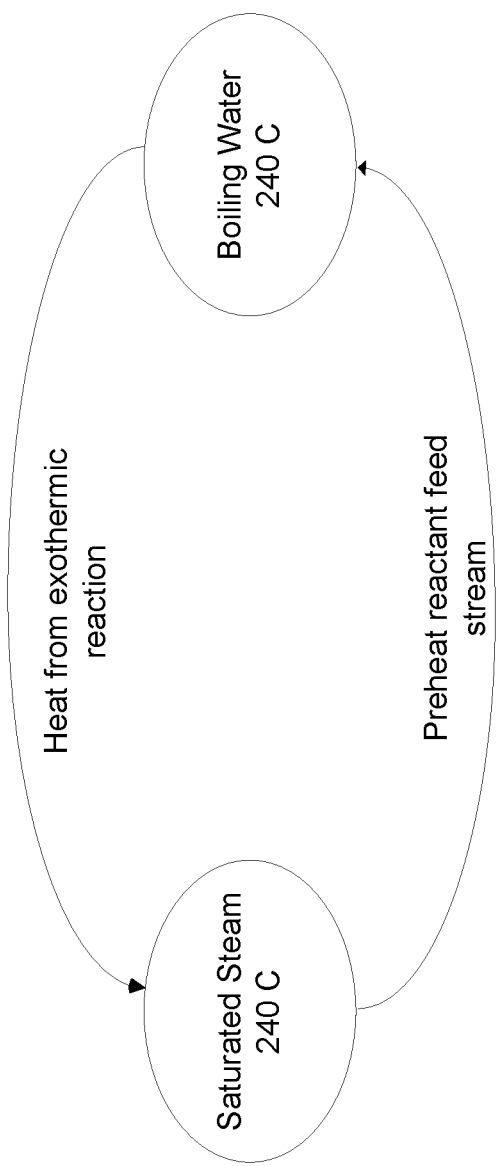
FIG. 3 shows an example of a high-level diagram of a heat integration loop employing saturated steam.

FIG. 2 is a schematic flow chart of certain embodiments of a system 200 for producing acetic acid including recycle paths 202, 204, and 205. For ease of discussion, certain components of reactant and/or product streams, phase information, temperature, and pressure are not shown in FIG. 2 but are described further below. In the example of FIG. 2, water is fed to one or more $H_2O$ electrolyzers 206 to generate hydrogen gas. Other hydrogen sources may be used instead of or in addition to an $H_2O$ electrolyzer. Carbon dioxide is fed to one or more $CO_2$ electrolyzers 208 to generate carbon monoxide. As described further below, the product stream may include other components including hydrogen and/or unreacted carbon dioxide.

The $H_2$ and CO streams are mixed with a $CO/H_2$ recycle stream to provide a feed stream to the $CH_3OH$ synthesis reactor 210. Further description and examples of $CH_3OH$ synthesis reactors are provided below. In some embodiments, the methanol synthesis occurs at elevated pressure and temperature, with the feed stream components compressed and heated appropriately.

Methanol is produced in the $CH_3OH$ synthesis reactor 210 and then separated from unreacted carbon monoxide and hydrogen at 212. The separation can involve condensing the methanol. The separated carbon monoxide and hydrogen are recycled in recycle path 202 including appropriate reheating and re-pressurization for reaction in the $CH_3OH$ synthesis reactor 210.

In some embodiments, carbon dioxide is present in the output of the one or more $CO_2$ electrolyzers 208. In such embodiments, water ($H_2O$) is a byproduct of the methanol synthesis reaction. The system 200 may include an absorber to separate the water from the methanol.

The output of the one or more $CO_2$ electrolyzers may be purified prior to entering the synthesis reactor(s) to form a purified CO stream. However, there may be trace amounts of other compounds, such as $CO_2$.

The separated methanol, recycled methanol from recycle path 204, recycled carbon monoxide from recycle path 205, and carbon monoxide from the one or more $CO_2$ electrolyzers 208 and are fed to the acetic acid ($CH_3CO_2H$) synthesis reactor 214. (Any of these streams may or may not be joined with one or more of the other streams prior to being fed to acetic acid synthesis reactor 214). Further description and examples of $CH_3CO_2H$ synthesis reactors are provided below. In some embodiments, the acetic acid synthesis occurs at elevated pressure and temperature, with the feed stream components compressed and heated appropriately.

Acetic acid is produced in the $CH_3CO_2H$ synthesis reactor 214. Carbon monoxide is separated from the methanol and acetic acid at 216. Acetic acid is then separated from unreacted methanol at 218. The separation can involve distillation. The separated carbon monoxide and methanol are recycled including appropriate reheating and re-pressurization for reaction in the $CH_3CO_2H$ synthesis reactor 214. Purified acetic acid is produced.

As discussed further below, both the methanol synthesis reaction and the acetic acid synthesis reaction are exothermic and are performed at elevated temperatures. A heat integration loop is employed to recover heat from the reactions, maintain temperature in the reactors and preheating reaction mixtures. Water cycles through the heat integration loop at a constant temperature, transitioning between saturated steam, boiling water, and/or a mixed phase of steam and water. Heat is absorbed or given off for preheating the reaction mixture and maintaining the reaction temperature. FIG. 3 shows an example of a high-level diagram of a heat integration loop employing saturated steam. (In the example of FIG. 3, saturated steam is 240° C. at about 33 bar. However, the pressure and associated temperature may vary depending on the particular reactor.) Heat from an exothermic reaction is used to convert boiling water to saturated steam. That is then used to preheat the reactant feed stream converting the saturated steam to boiling water. The temperature of the saturated steam and boiling water is held constant in the heat integration loop. An example of heat integration loop incorporating methanol synthesis and acetic acid synthesis reactions is described below with respect to FIGS. 4A and 4B.

According to various embodiments, the methanol synthesis reactor 210 may be a fixed packed bed tubular reactor. The molar ratio of CO to $H_2$ is 1:2. In some embodiments, a Cu—ZnO catalyst is used. Other examples of catalysts include those containing ruthenium, iridium, palladium, magnesium, and aluminum. In some embodiments, reaction pressure may range from 60 to 100 bar and reaction temperature from 200° C. to 280° C., and in some embodiments, from 200° C. to 250° C. The selectivity depends on the catalyst, reaction pressure and temperature.

According to various embodiments, the acetic acid synthesis reactor 214 may be a fixed packed bed tubular reactor. The molar ratio of CO to $CH_3OH$ is 1:1. Byproducts can include dimethyl ether and methyl acetate. In some embodiments, a catalyst highly selective to acetic acid formation is used. An example of such a catalyst is $ReO_4/SiO_2$ catalyst. Ruthenium- and/or iridium-containing catalysts may also be used. Additional catalysts include nickel iodides and copper-nickel-palladium (Cu—Ni—Pd) catalysts. Reaction pressure may range from 10 bar to 350 bar, e.g., 10 bar to 100 bar, and reaction temperature from 130° C. to 320° C., e.g., 200° C. to 280° C. The selectivity depends on reaction pressure and temperature and can be over 97%. A reaction temperature of close to or at least 250° C. to achieve high selectivity and avoid forming byproducts, particularly dimethyl ether.

Aspects of the systems and methods disclosed herein are described below with reference to FIGS. 4A and 4B, which show an example of a system for acetic acid production. For the purposes of description, a methanol synthesis reaction temperature and pressure of 250° C. and 100 bar, respectively, are described. Similarly, for the purposes of description, an acetic acid synthesis reaction temperature and pressure of 250° C. and 40 bar, respectively, are described. However, the description may be applied to other reaction conditions.

Figure 4A:
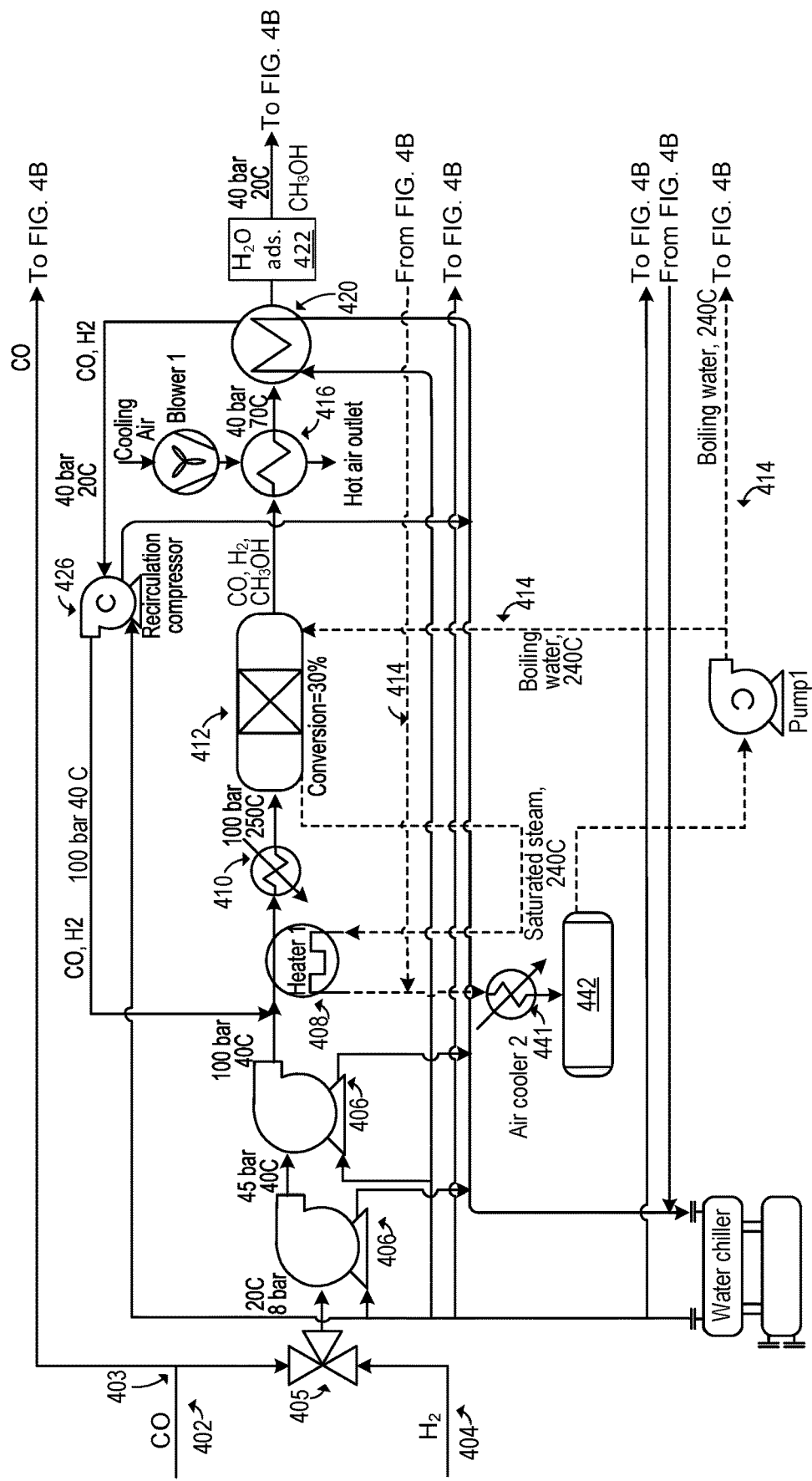
FIGS. 4A and 4B depicts an example of a system for producing acetic acid.

Turing to FIG. 4A, incoming CO and $H_2$ streams are shown at 402 and 404, respectively. The CO stream is split at a junction 403, with half input to the acetic acid synthesis reactor (shown in FIG. 4B) and half mixed with $H_2$ at 405 to form a reaction mixture for methanol synthesis.

The CO stream 402 is an output of one or more $CO_2$ electrolyzers. $CO_2$ electrolyzers configured to produce CO are described further below. In alternate embodiments, different CO electrolyzers are used to supply CO for methanol synthesis and acetic acid synthesis. The $H_2$ stream 404 may be an output of one or more water electrolyzers.

As received, the CO and $H_2$ streams may be at relatively low pressure and temperature. In the example of FIG. 4A, the reaction mixture is at 20° C. and 8 bar and undergoes pressurization and heating prior to reaction. One or more compressors 406 are connected in series to compress the reaction mixture to the reaction pressure. Some heating occurs as an effect of the compression. In the example of FIG. 4A, the reaction mixture is at 100 bar and 40° C. after pressurization. In other embodiments, the reaction mixture may be at a higher temperature, e.g., up to 100° C., as a result of the compression.

A CO/$H_2$ recycle stream at the same conditions is mixed with the CO/$H_2$ stream and is heated in a heat exchanger 408. The heat exchanger 408 exchanges heat from saturated steam as described above with respect to FIG. 3 and is part of a heat integration loop 414 (shown in dotted lines). The CO/$H_2$ feed stream is heated to a first elevated temperature. In some embodiments, an auxiliary heater is used to raise the temperature from the first elevated temperature to the reaction temperature. For example, the reactant feed may exit the heat exchanger 408 at 230° C. with the auxiliary heater 410 used to raise the temperature to 250° C. The auxiliary heater may be an electric heater that uses solar generated or other green electricity.

The heated, pressurized reactant feed stream is then inlet to the methanol synthesis reactor 412. This reactor may be an isothermal, fixed packed-bed tubular reactor, as described above.

The heat integration loop 414 is used to absorb heat generated in the reactor and maintain the reaction temperature. Boiling water at 240° C. absorbs the heat and is converted to saturated steam, which is then used in heat exchanger 408 to preheat the reaction mixture as described above.

In some embodiments, the conversion in the reactor may be less than 40%. In the example of FIG. 4A, the conversion is 30%, with a significant amount of carbon monoxide and hydrogen outlet from the methanol synthesis reactor 412 along with the synthesized methanol. The reaction is isothermal, with the outlet temperature approximately that of the inlet temperature (250° C. in the example of FIG. 4A). Pressure drop will depend on the particular characteristics of the reactor. In the example of FIG. 4A, it is 60 bar (pressure going from 100 bar to 40 bar), though the pressure drop may be smaller. The remaining processes may take place at this outlet pressure (or slightly lower pressures, considering a pressure drop associated with each system component) such that further pressurization of the reactant/outlet streams is not performed.

As described above, the CO and $H_2$ are separated from the methanol and recycled. Prior to separation, the outlet stream may be cooled using an air cooler 416 or other appropriate cooler. In the example of FIG. 4A, the outlet stream is cooled to 70° C. A condenser 420 is used to condense the methanol, separating it from the carbon monoxide and hydrogen. The condenser 420 may use chilled water as shown.

The carbon monoxide and methanol are re-pressurized in a recirculation compressor 426 to the reaction pressure for recycle. A pressure of 40 bar is shown in the example of FIG. 4A, though pressure drop across the methanol synthesis reactor 412 and resulting outlet pressure depends on various parameters such as porosity of the reactor bed and particle size. In some embodiments, the pressure may be much higher.

In some embodiments, carbon dioxide is present in an outlet of the one or more carbon dioxide electrolyzers and in the feed stream to the methanol synthesis reactor 412. If present, carbon dioxide reacts with hydrogen in the methanol synthesis reactor 412 to form water as a byproduct. For example, in some embodiments, at least 10%, or at least 20%, by weight, of the CO inlet stream 402 may be carbon dioxide that will be converted to water.

If present, the water will condense with the methanol and may be removed by a water removal adsorber 422, or by another appropriate method such as distillation. If the CO inlet stream 402 including $CO_2$ does not have contaminants, the water removed by the water removal absorber 422 may be recycled (not shown) to the water electrolyzer for electrolysis or as an input to the anode side of $CO_2$ electrolyzer as described further below.

Figure 4B:
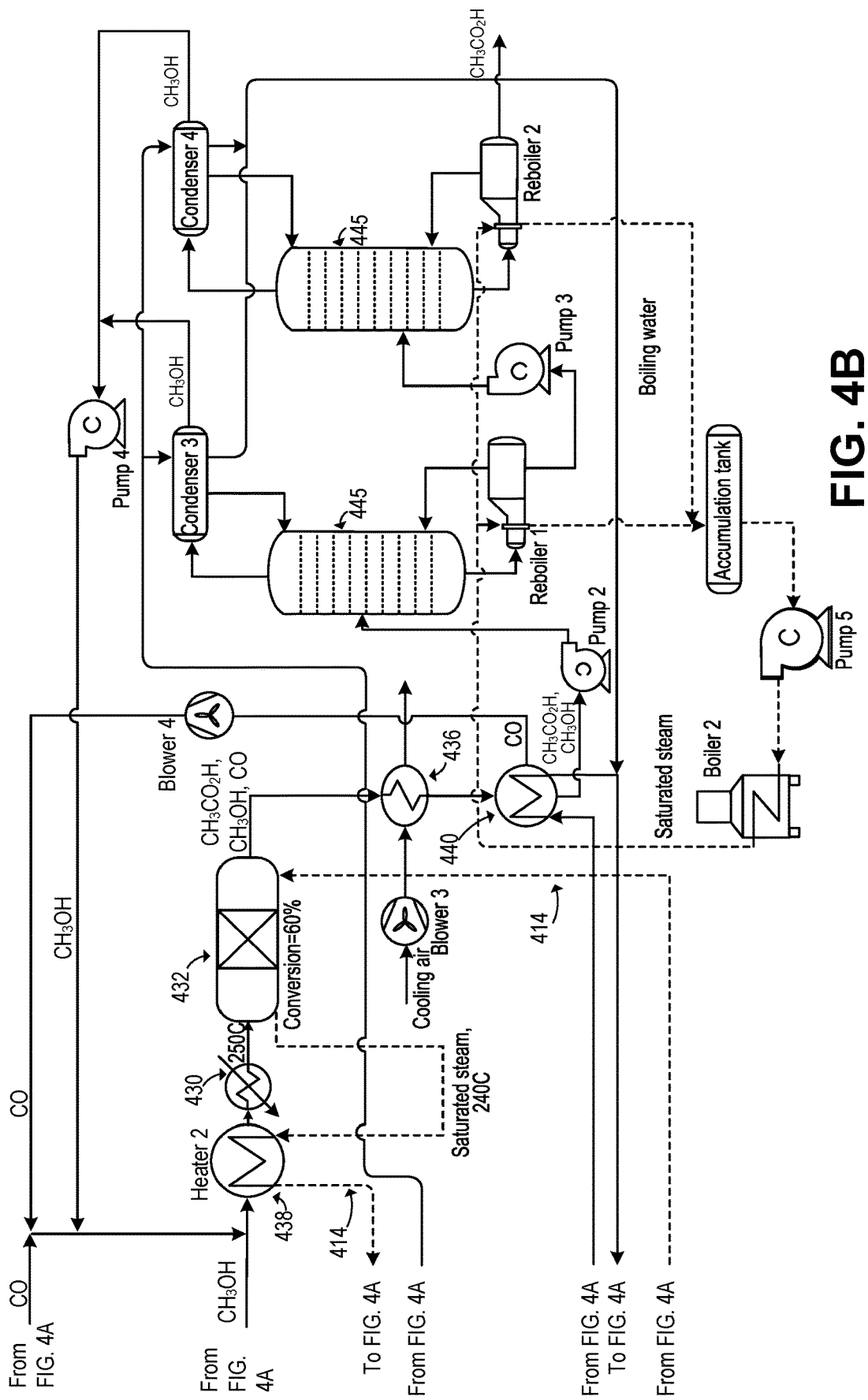

Turning to FIG. 4B, the purified methanol is mixed with carbon monoxide from the one or more carbon dioxide electrolyzers and recycled carbon monoxide to provide a feed stream for the acetic acid synthesis reactor of 432. A heat exchanger 438, part of the heat integration loop 414, preheats the acetic acid synthesis reactor feed stream. Saturated steam is converted to boiling water with the heat raising the temperature of the feed stream to a second elevated temperature. In some embodiments, an auxiliary heater is used to raise the temperature from the first elevated temperature to the reaction temperature. For example, the reactant feed may exit the heat exchanger 438 at 230° C. with the auxiliary heater 430 used to raise the temperature to 250° C. The auxiliary heater may be an electric heater that uses solar generated or other green electricity.

The heated reactant feed stream is then inlet to the acetic acid synthesis reactor 432. This reactor may be an isothermal, fixed packed-bed tubular reactor, as described above. In the example of FIG. 4B, the conversion is 60%, though the conversion may vary depending on the particular reactor and reaction kinetics. Dimethyl ether is a possible byproduct that is flammable and toxic. Formation of dimethyl ether should be avoided in the acetic acid synthesis reactor. A $ReO_4/SiO_2$ catalyst is highly selective to acetic acid and can be used to avoid dimethyl ether production.

The heat integration loop 414 is used to absorb heat generated in the reactor and maintain the reaction temperature. Boiling water at 240° C. absorbs the heat and is converted to saturated steam, which is then used in heat exchanger 438 to preheat the reaction mixture as described above.

In some embodiments, the saturated steam is not fully converted to liquid water in the heat exchangers 408 and/or 438. A mixture of steam and water may leave heat exchangers 408 and/or 438. An additional cooler 441 may be used to fully convert the steam/water mixture to liquid water. Cooler 441 may be an air cooler or any appropriate cooler. An accumulation tank 442 may be used to accumulate boiling water, with the cycle then repeated.

The temperature of the boiling water/saturated steam in the heat integration loop 414 is lower than the lowest reaction mixture temperature to allow the boiling water to absorb the reaction heat. For an acetic acid synthesis reaction temperature of 250° C., for example, a boiling water/saturated steam temperature of 240° C. may be used. That temperature difference (250° C. to 240° C.) presents the driving force for heat transfer in the reactor. For a heat integration loop temperature of 240° C., and assuming that the minimum temperature difference between a heat exchanger's hot and cold fluid is 10° C., the maximum achievable elevated temperature is 230° C. The first and second elevated temperatures, i.e., the temperatures that the feed streams reach from heating by the heat integration loop may be approximately the same or differ, e.g., by about 1 to 30° C. In the example of FIGS. 4A and 4B, the first and second elevated temperatures are 230° C. It is possible that the methanol feed stream may be heated to a lower elevated temperature, e.g., 200° C. However, the water/steam pressure and temperature of the heat integration loop 414 are the same for both reactors and auxiliary heaters. By having only one steam-water cycle instead of two, capital investment costs are significantly reduced. The higher the elevated temperature, the lower the power requirement and operating costs of a downstream electric heater.

In the example of FIG. 4B, the acetic acid synthesis reaction occurs at an intermediate pressure without pressurizing the feed stream prior to inlet to the acetic acid synthesis reactor 432. In other embodiments, one or more compressors may be used to increase pressure.

The outlet stream of the acetic acid synthesis reactor 432 includes unreacted methanol and carbon monoxide and synthesized acetic acid. As described above, the CO is separated from the methanol and acetic acid and recycled. Prior to separation, the outlet stream may be cooled using an air cooler 436 or other appropriate cooler. In the example of FIG. 4B, the outlet stream may be cooled to 70° C. A condenser 440 is used to condense the methanol and acetic acid, separating it from the carbon monoxide. The carbon monoxide is recycled for mixing with methanol and reaction in the acetic acid synthesis reactor 432. In the example shown, a blower is used for CO recycle. This is appropriate for a small pressure drop across the acetic acid synthesis reactor 432. However, in some embodiments, a compressor may be used instead of a blower as necessary to pressurize the recycle stream to about 40 bar or other operating pressure.

In some embodiments, some amount of $CO_2$ (originally from the electrolyzer) may be present in the outlet stream and will leave the condenser 440 in the gas phase, along with the CO.

The acetic acid may be separated from the methanol using one or more distillation columns 445, depending on the desired purity level of the acetic acid. The methanol is condensed and recycled as shown in FIG. 4B.

Carbon Dioxide Electrolyzer to Produce Carbon Monoxide

As described above, in some embodiments, carbon monoxide is produced by a carbon dioxide electrolyzer. In some embodiments, the carbon dioxide electrolyzer receives purified $CO_2$ from a carbon dioxide purifier that may be part of a system described herein. A carbon dioxide purifier may receive impure $CO_2$ that originates from any of various sources. Examples include air or other ambient gas, combustion output gases, and factory output such as output from a cement plant or a steelmaking plant. Combustion may occur in, for example, a turbine, engine, or other device that may be provided in stationary structure (e.g., a powerplant) or a mobile structure (e.g., a transportation vehicle). In certain embodiments, impure $CO_2$ is from tailpipe exhaust. Typically, though not necessarily, the $CO_2$ is provided to purifier in gaseous form. Examples of $CO_2$ purifiers are provided in U.S. Provisional Patent Application No. 63/366,901, titled "$CO_2$ Purification with Electroactive Polymers," filed Jun. 23, 2022, and incorporated by reference herein.

A carbon dioxide electrolyzer of the disclosure may be directly connected (e.g., via the cathode flow field and/or gas diffusion layer) to a downstream system (such as the acetic acid synthesis system described above), and/or the carbon dioxide reactor output may be connected to a purification system; a gas compression system; or both a purification system and a gas compression system, in either order; which then connects to an input of the downstream acetic acid synthesis system and/or to one or more storage devices. Multiple purification systems and/or gas compression systems may be employed. In various embodiments, a carbon-containing product and/or oxygen produced by a carbon oxide electrolyzer is provided to a storage vessel for the carbon-containing product and/or a storage vessel for the oxygen.

A $CO_2$ electrolyzer (optionally integrated with a $CO_2$ purifier) may be configured, designed, and/or controlled in a manner that allows the electrolyzer to produce one or more carbon dioxide electrolysis products in a quantity, concentration, and/or ratio suitable for any of various downstream processes such as producing valuable carbon-containing products such as acetic acid.

Different $CO_2$ electrolyzers (e.g., including different layer stacks, catalysts and/or catalyst layers, PEMs, flow fields, gas diffusion layers, cell compression configurations, and/or any other suitable aspects, etc.) can be used to produce different reduction products; however, different reduction products can additionally or alternatively be produced by adjusting the operation parameters, and/or be otherwise achieved.

In various embodiments, a $CO_2$ electrolyzer includes one or more cells each having a membrane electrode assembly (MEA). An MEA contains an anode catalyst layer, a cathode catalyst layer, electrolyte, and optionally one or more other layers. The layers may be solids and/or gels. The layers may include polymers such as ion-conducting polymers. Ion-conducting polymers may anion-conducting or cation-conducting according to various embodiments. An anion-conducting polymer may also be referred to as an anion-exchange membrane and a cation-conducting polymer may also be referred to as a cation-exchange membrane.

When in use, the cathode of an MEA promotes electrochemical reduction of $CO_2$ by combining three inputs: $CO_2$, ions (e.g., protons or hydroxide ions) that chemically react with $CO_2$, and electrons. The reduction reaction may produce CO, hydrocarbons, and/or hydrogen and oxygen-containing organic compounds such as methanol, ethanol, and acetic acid. When in use, the anode of an MEA promotes an electrochemical oxidation reaction such as electrolysis of water to produce elemental oxygen and protons. The cathode and anode may each contain catalysts to facilitate their respective reactions.

Figure 5:
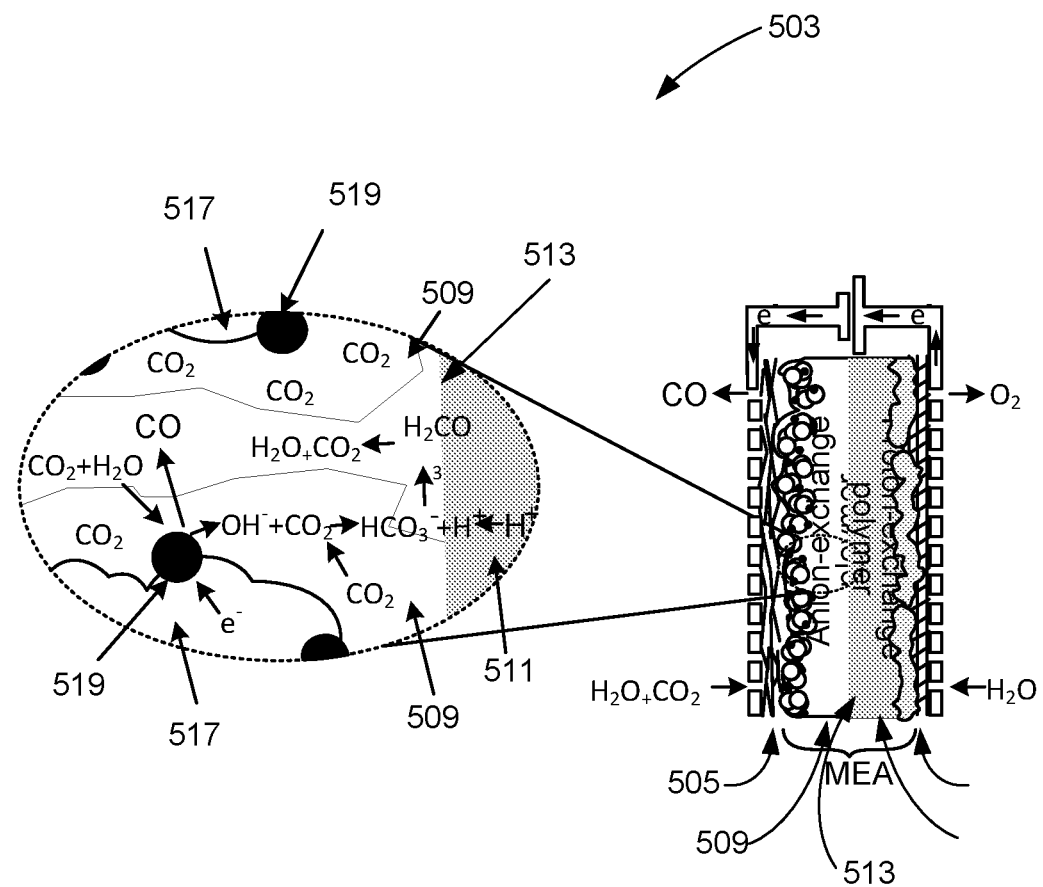
FIG. 5 shows an example of a $CO_2$ electrolyzer for producing carbon monoxide.

In particular embodiments, MEAs with bipolar membranes or those with anion exchange membranes (AEMs) may be used. FIG. 5 shows a $CO_2$ electrolyzer that includes a MEA having a bipolar membrane. $CO_2$ electrolyzer 503 is configured to receive water and $CO_2$ (e.g., humidified or dry gaseous $CO_2$) as a reactant at a cathode 505 and expel CO as a product. Electrolyzer 503 is also configured to receive water as a reactant at an anode 507 and expel gaseous oxygen. Electrolyzer 503 includes bipolar layers having an anion-conducting polymer 309 adjacent to cathode 505 and a cation-conducting polymer 511 (illustrated as a proton-exchange membrane) adjacent to anode 507.

As illustrated in the magnification inset of a bipolar interface 513 in electrolyzer 503, a cathode catalyst layer 505 includes an anion exchange polymer (which in this example is the same anion-conducting polymer 509 that is in the bipolar layers) electronically conducting carbon support particles 517, and metal nanoparticles 519 supported on the support particles. $CO_2$ and water are transported via pores such as pore 521 and reach metal nanoparticles 519 where they react, in this case with hydroxide ions, to produce bicarbonate ions and reduction reaction products (not shown). $CO_2$ may also reach metal nanoparticles 519 by transport within anion exchange polymer 515.

Hydrogen ions are transported from anode 507, and through the cation-conducting polymer 511, until they reach bipolar interface 513, where they are hindered from further transport toward the cathode by anion exchange polymer 509. At interface 513, the hydrogen ions may react with bicarbonate or carbonate ions to produce carbonic acid ($H_2CO_3$), which may decompose to produce $CO_2$ and water. The resulting $CO_2$ may be provided in gas phase and should be provided with a route in the MEA back to the cathode 505 where it can be reduced. The cation-conducting polymer 511 hinders transport of anions such as bicarbonate ions to the anode where they could react with protons and release $CO_2$, which would be unavailable to participate in a reduction reaction at the cathode.

As illustrated, a cathode buffer layer having an anion-conducting polymer may work in concert with the cathode and its anion-conductive polymer to block transport of protons to the cathode. While MEAs employing ion conducting polymers of appropriate conductivity types in the cathode, the anode, cathode buffer layer, and if present, an anode buffer layer may hinder transport of cations to the cathode and anions to the anode, cations and anions may still come in contact in the MEA's interior regions, such as in the membrane layer.

As illustrated in FIG. 5, bicarbonate and/or carbonate ions combine with hydrogen ions between the cathode layer and the anode layer to form carbonic acid, which may decompose to form gaseous $CO_2$. It has been observed that MEAs sometime delaminate, possibly due to this production of gaseous $CO_2$, which does not have an easy egress path.

The delamination problem can be addressed by employing a cathode buffer layer having pores. One possible explanation of its effectiveness is that the pores create paths for the gaseous carbon dioxide to escape back to the cathode where it can be reduced. In some embodiments, the cathode buffer layer is porous but at least one layer between the cathode layer and the anode layer is nonporous. This can prevent the passage of gases and/or bulk liquid between the cathode and anode layers while still preventing delamination. For example, the nonporous layer can prevent the direct passage of water from the anode to the cathode.

The cathode catalyst layer of the MEA includes a catalyst configured for production of CO or other desired product. A catalyst configured for CO has a propensity to catalyze one or more CO production reactions preferentially over other reactions. Gold (Au), for example, may be used to catalyze carbon monoxide (CO) production. The conformation of the catalyst layer may be engineered to achieve desired CO production characteristics for the MEA. Conformation characteristics such as thickness, catalyst loading, and catalyst roughness can affect desired product production rate, desired production selectivity (e.g., selectivity of CO over other potential products, such as hydrogen, methane, etc.), and/or any other suitable characteristics of carbon dioxide reactor operation.

Examples of cathode catalyst layers for CO production include:

Au nanoparticles 4 nm in diameter supported on Vulcan XC72R carbon and mixed with TM1 anion exchange polymer electrolyte from Orion. Layer is about 15 μm thick, Au/(Au+C)=30%, TM1 to catalyst mass ratio of 0.32, mass loading of 1.4-1.6 mg/cm2, estimated porosity of 0.47

Au nanoparticles 45 nm in diameter supported on Vulcan XC72R carbon and mixed with TM1 anion exchange polymer electrolyte from Orion. Layer is about 11 micron thick, Au/(Au+C)=60%. TM1 to catalyst mass ratio of 0.16, mass loading of 1.1-1.5 mg/cm2, estimated porosity of 0.41 in the catalyst layer.

Au nanoparticles 4 nm in diameter supported on Vulcan XC72R carbon and mixed with TM1 anion exchange polymer electrolyte from Orion. Layer is about 25 micron thick, Au/(Au+C)=20%. TM1 to catalyst mass ratio of 0.32, mass loading of 1.4-1.6 mg/cm2, estimated porosity of 0.54 in the catalyst layer.

The $CO_2$ electrolyzer is not limited to those having bipolar membranes. An MEA with only a cation exchange membrane or an anion exchange membrane between the cathode catalyst layer and the anode catalyst layer may be used.

Running the electrolyzer can include providing one or more inputs (e.g., gasses, liquids, solids, etc.), such as carbon dioxide, carbon monoxide, a carbon oxide source (e.g., waste gas), and/or water; causing all or some of the inputs to undergo reactions (e.g., by applying a voltage across the device electrodes), thereby generating products; and/or removing the products from the electrolyzer (e.g., as an output gas stream). Such reactions can include, for example, reducing carbon dioxide and/or water to generate products such as CO (and/or other carbon-containing products (CCPs) and/or $H_2$. However, running the electrolyzer can additionally or alternatively include causing any other suitable reactions to occur, and/or can additionally or alternatively include any other suitable elements performed in any suitable manner.

In some embodiments, a desired set of process conditions such as process conditions known to result in a desired output metric value (e.g., a desired $CO:H_2$ ratio) are used. The method can additionally or alternatively include altering process conditions, such as based on a difference between actual and desired outputs (e.g., to reduce or eliminate the difference). For example, the method can include: imposing an initial set of process conditions; monitoring one or more output metrics (e.g., $CO:H_2$ ratio); determining that an output metric differs from a target output metric (e.g., is greater than or less than the target); altering one or more process conditions to reduce the output metric difference (e.g., reducing or increasing a process condition value, such as a condition for which the output metric tends to increase or decrease along with an increasing process condition value); and optionally continuing to monitor the output metrics and/or alter the process conditions (e.g., implementing a closed-loop control of the process conditions based on the output metrics).

Under some conditions, the method may achieve carbon dioxide conversion (e.g., CO fractional yield) greater than 95% (e.g., up to 100%), such as wherein the system, run under such conditions, can achieve at least the threshold conversion metric. However, the method can additionally or alternatively include achieving carbon dioxide conversion greater than 50%, 60%, 70%, 80%, 90%; between 10%-100%, such as 10-40, 30-50, 40-60, 50-70, 60-75, 70-85, 80-95, 90-95, 92-98, and/or 95-100%; and/or any other suitable carbon dioxide conversion.

The electrolyzer products (or a subset thereof) can be provided to a downstream consumer of the products as described above. The method can optionally include altering the electrolyzer products after they are produced and prior to providing them to downstream consumer. Altering the electrolyzer products can optionally include purifying the products (e.g., removing impurities, such as $SO_x$ and/or NOx, from a reactor output stream). Altering the electrolyzer products can additionally or alternatively include mixing additional gasses (and/or other substances) into an electrolyzer output stream (and/or input stream), such as to achieve a desired output metric. In one variation, if the $CO:H_2$ ratio of the electrolyzer output differs from a desired value, the ratio can be adjusted by mixing the electrolyzer output with other gasses (e.g., substantially pure CO and/or $H_2$; another mixture of CO and $H_2$, such as previously produced and stored outputs of the electrolyzer, the output of a second electrolyzer, outputs and/or waste gasses of other systems, etc.). For example, the $CO:H_2$ ratio of the output stream (and/or gasses in any other portion of the electrolyzer) can be monitored (e.g., continuously during electrolyzer production), and deviations from the desired value can be compensated for by mixing in other gasses (e.g., adding CO and/or a CO-rich mixture to increase the ratio, adding $H_2$ and/or an $H_2$-rich mixture to decrease the ratio). This example may also include altering the process conditions in order to correct the electrolyzer outputs.

Electrolyzer process conditions can include, e.g., input carbon dioxide flow rate and/or pressure, input gas hydration, current density, voltage (e.g., maintained between about 1.5 V and 3 V, additionally or alternatively operated at less than about 1.5 V, between about 2 V-2.5 V, between about 2 V-4 V, greater than about 4 V, and/or at any other suitable voltage(s)), and/or temperature. The process conditions can additionally or alternatively include system configurations, such as gas diffusion layer aspects, catalyst aspects, flow field aspects, and/or PEM aspects. However, any other suitable process condition can be controlled or targeted. The process condition can be uncontrolled (e.g., dictated by an upstream system), controlled to meet a target value (e.g., wherein the target value can be determined based on the application receiving the reactor output, the instantaneous or anticipated reactor operation parameters, or otherwise determined), or otherwise determined.

The process conditions may include a pressure (e.g., input gas pressure, electrolyzer pressure, etc.) greater than atmospheric pressure (e.g., within and/or greater than a threshold pressure range, such as about 1-5, about 5-10, about 10-20, about 20-50, about 50-100, about 100-300, about 300-1000, about 1-10, about 5-50, about 10-100, about 20-500, and/or greater than about 1000 atm, about 14-50, about 50-150, about 100-300, about 200-500, about 500-1000, about 750-1500, about 1000-3000, about 3000-10,000, about 10,000-20,000, and/or greater than about 20,000 psi, etc.) and/or greater than pressures typically feasible in electrolyzers other than gas-phase electrolyzers, but can additionally or alternatively include pressures substantially equal to 1 atmosphere, less than about 1 atmosphere, and/or any other suitable pressures. The process conditions may include a temperature (e.g., reactor temperature) greater than typical room temperature (e.g., within and/or greater than a threshold temperature range, such as about 25-50, about 40-60, about 50-100, about 50-75, about 70-100, and/or greater than about 100° C., etc.) and/or greater than temperatures typically feasible in electrolyzers other than gas-phase electrolyzers, but can additionally or alternatively include temperatures substantially equal to room temperature (e.g., about 20-30° C.), less than room temperature, and/or any other suitable temperatures. However, the process conditions can additionally or alternatively include any other suitable process conditions.

A higher carbon dioxide flow rate can lead to increased production of CCPs such as CO (e.g., due to greater availability of carbon dioxide for reduction), and thus an increased CCP:$H_2$ ratio (and correspondingly, lower carbon dioxide flow rate can lead to decreased CCP production and CCP:$H_2$ ratio). In some embodiments, higher carbon dioxide flow rate can also result in reduced carbon dioxide conversion efficiency, thereby diluting the output stream (e.g., syngas output) with unreacted carbon dioxide. For example, carbon dioxide flow rate (e.g., measured at the reactor inlet) can be maintained at one or more values in the range of about 0.1-1000 sccm/cm2 (e.g., about 0.1-1, about 1-10, about 10-100, and/or about 100-1000 sccm/cm2).

In a first specific example of control based on input gas flow rate, electrolyzer configuration A with a triple serpentine flow field is used, electrolyzer pressure is substantially maintained at 120 psi, current density is substantially maintained at 500 mA/cm2, and electrolyzer temperature is substantially maintained at 30° C. In this specific example, substantially pure carbon dioxide gas is input at various flow rates, wherein input flow rates (e.g., measured at the reactor inlet) of 12 sccm/cm$^2$, 20 sccm/cm2, and 40 sccm/cm2 result in CO:$H_2$ ratios of approximately 1:1, 2:1.1, and 4:1, respectively.

In a second specific example of control based on input gas flow rate, electrolyzer configuration A with a serpentine flow field is used, electrolyzer pressure is substantially maintained at 130 psi, and current density is substantially maintained at 500 mA/cm2. In this specific example, substantially pure carbon dioxide gas input at a 40 sccm/cm2 flow rate results in a CO:$H_2$ ratio of approximately 8:2, whereas a 12 sccm/cm2 flow rate results in an approximately 1:1 ratio.

Higher carbon dioxide pressure can lead to increased CCP fractional yield and/or CCP:$H_2$ ratio (and correspondingly, lower carbon dioxide pressure can lead to decreased CCP fractional yield and/or CCP:$H_2$ ratio). First, increased carbon dioxide pressure can result in greater availability of carbon dioxide for reduction, thereby increasing the total production of CCPs. Second, higher pressure at the catalyst can reduce water ingress to the catalyst (e.g., from the cathode), thereby lowering the amount of water available for reduction, which can directly increase the CCP:$H_2$ ratio and/or can reduce competition for catalyst reaction sites and/or reaction energy (e.g., thereby favoring reduction of carbon dioxide). Thus, in some embodiments (e.g., in which high CCP fractional yield and/or CCP:$H_2$ ratio is desired), high electrolyzer pressure (e.g., greater than 100 psi, up to but no greater than a carbon dioxide phase transition pressure, such as a critical pressure of 1070 psi, etc.) may be employed. For example, electrolyzer pressure can be maintained at one or more values in the range of about 1-1100 psi (e.g., about 1-10, about 10-100, about 100-300, about 200-600, and/or about 500-1100 psi), and/or at any other suitable pressure.

In a specific example of control based on electrolyzer pressure, electrolyzer configuration A with a single serpentine flow field is used, substantially pure carbon dioxide gas is input at about 100 sccm/cm$^2$, current density is substantially maintained at about 150 mA/cm$^2$, and electrolyzer temperature is substantially maintained at about 20° C. In this specific example, electrolyzer pressure is substantially maintained at various pressures, wherein electrolyzer pressures of 25, 50, 75, and 100 psi result in CO:$H_2$ ratios of approximately 3:2, 2.4:1, 3:1, and 5:1 and CO fractional yields of approximately 59%, 69%, 75%, and 84%, respectively.

Increasing input gas hydration can lead to increased water reduction (e.g., due to greater availability of water for reduction), and thus to a decreased CCP:$H_2$ ratio. For a substantially pure carbon dioxide input, only small amounts of water reach the catalyst (coming almost exclusively from the cathode side of the reactor), leading to a higher CCP:$H_2$ ratio. In contrast, when hydrated input gas is used, significant amounts of water from the input gas can reach the catalyst and react. For example, input gas hydration (e.g., proportion of water vapor in the input gas) can be maintained at one or more values in the range of 0% (e.g., substantially pure carbon dioxide, substantially unhydrated input gas) to 100% (e.g., 0-1, 1-3, 3-5, 5-7, 7-10, 10-15, 15-25, 25-50, 50-75, and/or 75-100 percent).

In a specific example of control based on input gas hydration, electrolyzer configuration A with a single serpentine flow field is used, current density is substantially maintained at 50 mA/cm$^2$, electrolyzer pressure is substantially maintained at 12 psi, and electrolyzer temperature is substantially maintained at 20° C. In this specific example, carbon dioxide gas with varying amounts of hydration is input at 100 sccm/cm$^2$, wherein pure carbon dioxide input gas results in a CO:$H_2$ ratio of approximately 3:2, input gas with 12.2% hydration results in a CO:$H_2$ ratio of approximately 1:5.67, and intermediate hydration amounts result in CO:$H_2$ ratios between these two values.

Electrolyzers can exhibit different regimes of CCP and $H_2$ production with respect to current density. In an idealized electrolyzer, at low current densities, no water reduction occurs and all current goes to reducing carbon dioxide, resulting in a substantially linear dependence of CO production on current and substantially no $H_2$ production; whereas at higher current densities, additional current (e.g., above a threshold current at which substantially all carbon dioxide is already being consumed) is used to reduce water, resulting in a substantially linear dependence of $H_2$ production on the additional current and substantially constant CO production. In many typical electrolyzer, these idealities are loosened, but the two general regimes are still exhibited: CO production increases much faster than $H_2$ production in the low current density regime, then approaches a plateau in the higher current density regime while $H_2$ production increases more rapidly. The method can include controlling CO and/or $H_2$ production (e.g., controlling CO:$H_2$ ratio) by operating at any or all of a wide range of current densities (e.g., controlling the electrolyzer operation within the low and/or high current density regime, etc.). In some embodiments, the use of gas phase input carbon dioxide can enable relatively high current densities (whereas electrolyzers using aqueous carbon dioxide may be limited to current densities of tens of mA/cm$^2$ or less). For example, the method can include operating at current densities between about 1 mA/cm$^2$ and 100 A/cm$^2$ (e.g., about 1-75 mA/cm$^2$, about 50-100 mA/cm$^2$, about 100-200 mA/cm$^2$, about 200-500 mA/cm$^2$, about 500-1000 mA/cm$^2$, about 50-1000 mA/cm$^2$, about 0.5-10 A/cm$^2$, about 1-2 A/cm$^2$, about 2-5 A/cm$^2$, about 5-10 A/cm$^2$, about 5-100 A/cm$^2$, about 10-20 A/cm$^2$, about 20-50 A/cm$^2$, about 50-100 A/cm$^2$, etc.; at, above, or below a threshold value such as about 50 mA/cm$^2$, about 65 mA/cm$^2$, about 80 mA/cm$^2$, about 90 mA/cm$^2$, about 100 mA/cm$^2$, about 110 mA/cm$^2$, about 120 mA/cm$^2$, about 130 mA/cm$^2$, about 140 mA/cm$^2$, about 150 mA/cm$^2$, about 200 mA/cm$^2$, about 300 mA/cm$^2$, about 500 mA/cm$^2$, about 700 mA/cm$^2$, about 1000 mA/cm$^2$, about 1500 mA/cm$^2$, etc.) and/or at any other suitable current densities.

In some embodiments, increased electrolyzer temperature can result in a reduced $CO:H_2$ ratio (e.g., due to increased ingress of water from the cathode, increased reactivity of water, etc.). The method can include controlling electrolyzer temperature within an operation range, such as a range between a minimum temperature (e.g., a water freezing temperature such as 0° C.) and a maximum temperature (e.g., about 40° C., about 50° C., about 60° C., about 75° C., etc.; a water boiling temperature such as 100° C.), in order to control $CO:H_2$ ratio and/or any other suitable output metrics.

In a specific example of control based on electrolyzer temperature, electrolyzer configuration A with a quadruple serpentine flow field is used, substantially pure carbon dioxide gas is input at 70 sccm/cm$^2$, current density is substantially maintained at 150 mA/cm$^2$, and electrolyzer pressure is substantially maintained at 100 psi. In this specific example, electrolyzer temperature is substantially maintained at various temperatures, wherein electrolyzer temperatures of 26.7, 35, 38.7, and 41.9° C. result in $CO:H_2$ ratios of approximately 1:0.4, 2:1, 1:1.8, and 1:3, respectively.

Characteristics of a gas diffusion layer (GDL) can additionally or alternatively be used to affect CCP and/or $H_2$ production. For example, the GDL hydrophobicity can alter $H_2$ production (e.g., by affecting water transport), wherein a more hydrophilic GDL favors $H_2$ production (thereby reducing the CCP:$H_2$ ratio) and a more hydrophobic GDL inhibits $H_2$ production (thereby increasing the CCP:$H_2$ ratio). Other GDL characteristics, such as thickness and/or pore size, can also be used to alter the reactor output.

Characteristics of the membrane (e.g., polymer electrolyte membrane) can additionally or alternatively be used to affect CCP and/or $H_2$ production. In examples, an anion exchange membrane, which favors CCP production, can be used to achieve high CCP:$H_2$ ratios, a cation exchange membrane, which favors $H_2$ production, can be used to achieve low CCP:$H_2$ ratios, and hybrid membranes (e.g., enabling both anion and cation transport) exhibiting various anion and cation transport characteristics (e.g., mobilities) can be used to achieve various intermediate ratios (e.g., membranes favoring anion transport for higher ratios, membranes favoring cation transport for lower ratios).

Characteristics of the catalysts (e.g., particle size, catalyst species, etc.) can additionally or alternatively be used to affect CCP and/or $H_2$ production. For example, larger catalyst particles can result in poor carbon dioxide transport, thereby inhibiting CCP production and reducing the CCP:$H_2$ ratio, whereas smaller catalyst particles can favor CCP production, thereby increasing the ratio. The relative number of active sites with high turnover frequency for hydrogen evolution ("hydrogen sites") and those with high turnover frequency for carbon dioxide reduction ("carbon dioxide sites") can additionally or alternatively be dependent on catalyst particle size: larger catalyst particles typically have a higher ratio of hydrogen sites to carbon dioxide sites, favoring $H_2$ production, whereas smaller catalyst particles typically have a lower ratio, favoring CO production. The catalyst type (e.g., catalyst species) can additionally or alternatively be used to control the electrolyzer output, such as by employing a mixture of one or more catalyst materials, wherein a first set of catalyst materials (e.g., gold) favor carbon dioxide reduction and a second set of catalyst materials (e.g., platinum) favor water reduction. In examples, a substantially pure gold catalyst can be used to achieve high CCP:$H_2$ ratios, a substantially pure platinum catalyst can be used to achieve low CCP:$H_2$ ratios, and gold-platinum mixtures (e.g., alloyed particles, mixtures of gold particles and platinum particles, etc.) of varying composition can be used to achieve various intermediate ratios (e.g., more gold for higher ratios, more platinum for lower ratios). The catalyst can additionally or alternatively include V, Cr, Mn, Fe, Co, Ni, Cu, Sn, Zr, Nb, Mo, Ru, Rh, Pd, Ag, Cd, Hf, Ta, W, Re, Ir, Hg, Al, Si, In, Ga, Tl, Pb, Bi, Sb, Te, Sm, Tb, Ce, Nd, and/or combinations thereof. The catalyst can additionally or alternatively be associated with (e.g., attached to, supported by, embedded in, adjacent, in contact with, etc.) one or more support structures (e.g., support particles, support matrix, etc.), which may be conductive support structures such as carbon, boron-doped diamond, and/or fluorine-doped tin oxide. However, the catalyst can additionally or alternatively include any other suitable materials.

In a specific example of control based on catalyst particle size, variations of electrolyzer configuration A with two catalyst particle sizes are used, both with electrolyzer temperature substantially maintained at 30° C., electrolyzer pressure substantially maintained at 100 psi, an interdigitated flow field, substantially pure carbon dioxide gas input at 10 sccm/cm$^2$, and current density substantially maintained at 500 mA/cm$^2$. The first set of catalyst particles have a characteristic size of 4 nm (as in the standard reactor configuration A), resulting in an HCR of 1:1.6 and a voltage of 3.8 V. The second set of catalyst particles have a characteristic size of 20 nm, resulting in an HCR of 1:2.8 and a voltage of 4.2 V.

Characteristics of electrolyzer cell compression can additionally or alternatively be used to affect CCP and/or $H_2$ production. In a specific example of control based on electrolyzer cell compression, electrolyzer configuration A is used with two different gasket thicknesses (resulting in greater compression for a larger gasket thickness), both with electrolyzer temperature substantially maintained at 30° C., electrolyzer pressure substantially maintained at 100 psi, a triple serpentine flow field, substantially pure carbon dioxide gas input at 40 sccm/cm$^2$, and current density substantially maintained at 500 mA/cm$^2$. The first gasket is 0.012 inches thick, resulting in an HCR of 1:4 and a voltage of 3.6 V. The second gasket is 0.010 inches thick, resulting in an HCR of 1:10.1 and a voltage of 3.8 V.

Characteristics of the flow field can additionally or alternatively be used to affect CCP and/or $H_2$ production. In a first specific example of control based on flow field characteristics, electrolyzer configuration A is used under two different sets of process conditions, both with electrolyzer temperature substantially maintained at 30° C. and electrolyzer pressure substantially maintained at 120 psi. In the first set of conditions, an interdigitated flow field is used, substantially pure carbon dioxide gas is input at 10 sccm/cm$^2$, and current density is substantially maintained at 160 mA/cm$^2$, resulting in a CO:H$_2$ ratio of 1.6:1. In the second set of conditions, a quadruple serpentine flow field is used, substantially pure carbon dioxide gas is input at 40 sccm/cm$^2$, and current density is substantially maintained at 120 mA/cm$^2$, resulting in a CO:H$_2$ ratio of 18.5:1.

In a second specific example of control based on flow field characteristics, electrolyzer configuration A is used under two different sets of process conditions, both with electrolyzer temperature substantially maintained at 30° C., electrolyzer pressure substantially maintained at 100 psi, substantially pure carbon dioxide gas input at 40 sccm/cm$^2$, and current density is substantially maintained at 500 mA/cm$^2$. In the first set of conditions, an interdigitated flow field is used and a voltage of 3.6 V is substantially maintained, resulting in a CO:H$_2$ ratio of 1.6:1. In the second set of conditions, a triple serpentine flow field is used and a voltage of 3.8 V is substantially maintained, resulting in a CO:H$_2$ ratio of 10.1:1.

However, any other suitable flow field can additionally or alternatively be employed to control the electrolyzer outputs, the process conditions can additionally or alternatively include any other suitable electrolyzer conditions, and the method can additionally or alternatively include controlling the electrolyzer output in any suitable manner.

Figure 6:
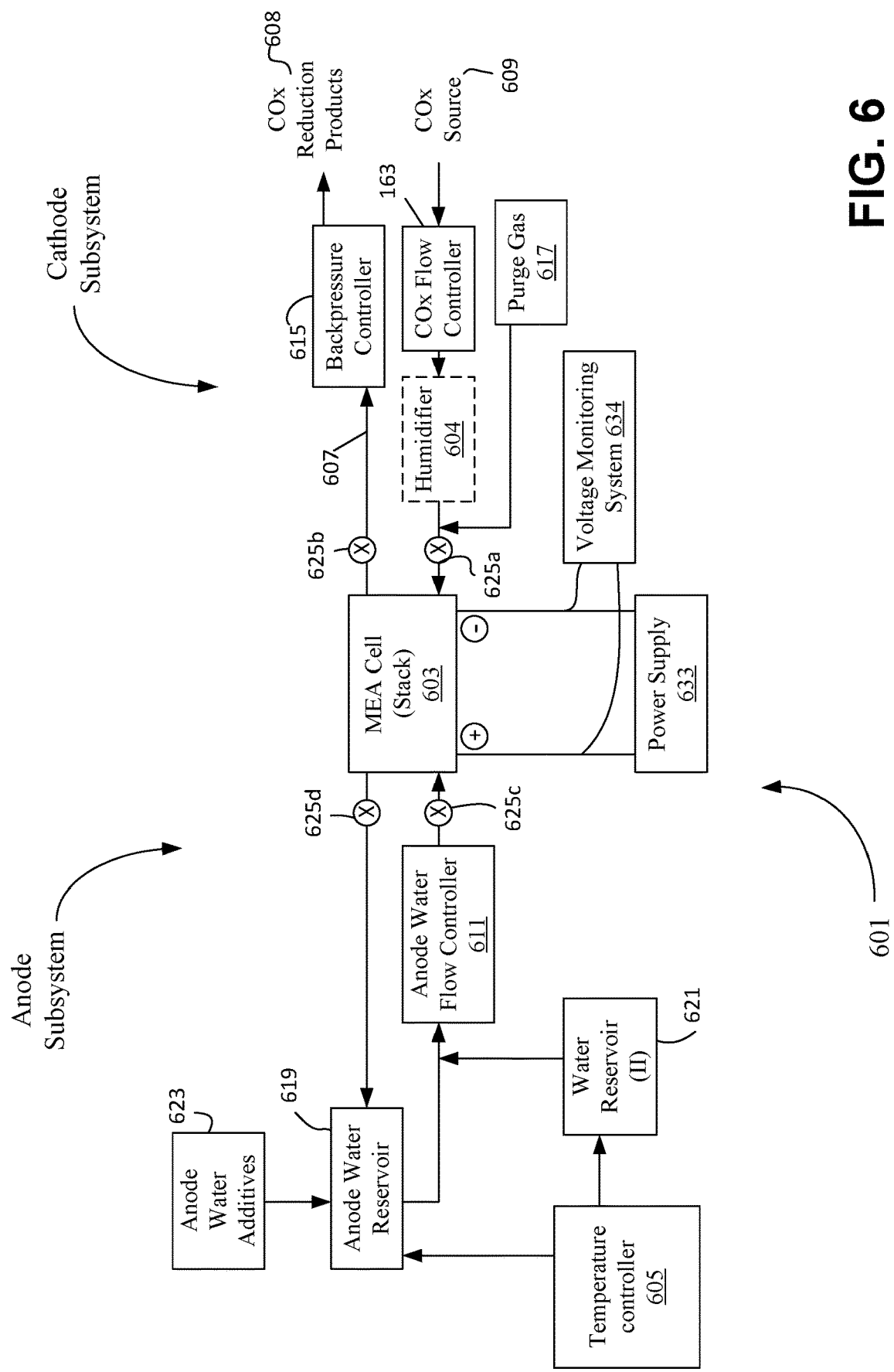
FIG. 6 depicts an example system for a carbon dioxide electrolyzer.

FIG. 6 depicts an example system 601 for a carbon dioxide reduction reactor 603 (often referred to as an electrolyzer herein) that may include a cell comprising a MEA. The reactor may contain multiple cells or MEAs arranged in a stack. System 601 includes an anode subsystem that interfaces with an anode of reduction reactor 603 and a cathode subsystem that interfaces with a cathode of reduction reactor 603. System 601 is an example of a system that may be used with or to implement any of the methods or operating conditions described herein for carbon dioxide electrolysis.

As depicted, the cathode subsystem includes a carbon dioxide source 609 configured to provide a feed stream of carbon dioxide to the cathode of reduction reactor 603, which, during operation, may generate an output stream that includes product(s) of a reduction reaction at the cathode. For the systems described herein, the product is or includes carbon monoxide as described above. The product stream may also include unreacted carbon dioxide and/or hydrogen. See 608.

The carbon dioxide source 609 is coupled to a carbon dioxide flow controller 613 configured to control the volumetric or mass flow rate of carbon dioxide to reduction reactor 603. One or more other components may be disposed on a flow path from flow carbon dioxide source 609 to the cathode of reduction reactor 603. For example, an optional humidifier 504 may be provided on the path and configured to humidify the carbon dioxide feed stream.

Humidified carbon dioxide may moisten one or more polymer layers of an MEA and thereby avoid drying such layers. Another component that may be disposed on the flow path is a purge gas inlet coupled to a purge gas source 617. In certain embodiments, purge gas source 617 is configured to provide purge gas during periods when current is paused to the cell(s) of reduction reactor 603. In some implementations, flowing a purge gas over an MEA cathode facilitates recovery of catalyst activity and/or selectivity. Examples of purge gases include carbon dioxide, carbon monoxide, hydrogen, nitrogen, argon, helium, oxygen, and mixtures of any two or more of these.

In various embodiments, a CO$_2$ purifier (not shown in FIG. 6) is provided upstream of source 609. Such CO$_2$ purifier may be considered to be part of the cathode subsystem.

During operation, the output stream from the cathode flows via a conduit 607 that connects to a backpressure controller 615 configured to maintain pressure at the cathode side of the cell within a defined range (e.g., about 50 to 800 psig, depending on the system configuration). The output stream may provide the reaction products 408 to one or more components (not shown) for separation and/or concentration.

In certain embodiments, the cathode subsystem is configured to controllably recycle unreacted carbon dioxide from the outlet stream back to the cathode of reduction reactor 603. In some implementations, the output stream is processed to remove reduction product(s) and/or hydrogen before recycling the carbon oxide. Depending upon the MEA configuration and operating parameters, the reduction product(s) may be carbon monoxide, hydrogen, hydrocarbons such as methane and/or ethylene, oxygen-containing organic compounds such as formic acid, acetic acid, and any combinations thereof. In certain embodiments, one or more components, not shown, for removing water from the product stream are disposed downstream form the cathode outlet. Examples of such components include a phase separator configured to remove liquid water from the product gas stream and/or a condenser configured to cool the product stream gas and thereby provide a dry gas to, e.g., a downstream process when needed. In some implementations, recycled carbon oxide may mix with fresh carbon dioxide from source 609 upstream of the cathode. Not shown in FIG. 6 are one or more optional separation components that may be provided on the path of the cathode outlet stream and configured to concentrate, separate, and/or store the reduction product from the reduction product stream.

As depicted in FIG. 6, an anode subsystem is configured to provide an anode feed stream to an anode side of the carbon oxide reduction reactor 603. In certain embodiments, the anode subsystem includes an anode water source, not shown, configured to provide fresh anode water to a recirculation loop that includes an anode water reservoir 619 and an anode water flow controller 611. The anode water flow controller 611 is configured to control the flow rate of anode water to or from the anode of reduction reactor 603. In the depicted embodiment, the anode water recirculation loop is coupled to components for adjusting the composition of the anode water. These may include a water reservoir 621 and/or an anode water additives source 623. Water reservoir 621 is configured to supply water having a composition that is different from that in anode water reservoir 619 (and circulating in the anode water recirculation loop). In one example, the water in water reservoir 621 is pure water that can dilute solutes or other components in the circulating anode water. Pure water may be conventional deionized water even ultrapure water having a resistivity of, e.g., at least about 15 MOhm-cm or over 18.0 MOhm-cm. Anode water additives source 623 is configured to supply solutes such as salts and/or other components to the circulating anode water.

During operation, the anode subsystem may provide water or other reactant to the anode of reactor 603, where it at least partially reacts to produce an oxidation product such as oxygen. The product along with unreacted anode feed material is provided in a reduction reactor outlet stream. Not shown in FIG. 6 are one or more optional separation components that may be provided on the path of the anode outlet stream and configured to concentrate, separate, and/or store the oxidation product from the anode product stream.

Other control features may be included in system 601. For example, a temperature controller may be configured to heat and/or cool the carbon oxide reduction reactor 603 at appropriate points during its operation. In the depicted embodiment, a temperature controller 605 is configured to heat and/or cool anode water provided to the anode water recirculation loop. For example, the temperature controller 605 may include or be coupled to a heater and/or cooler that may heat or cool water in anode water reservoir 619 and/or water in reservoir 621. In some embodiments, system 601 includes a temperature controller configured to directly heat and/or cool a component other than an anode water component. Examples of such other components in the cell or stack and the carbon oxide flowing to the cathode.

In certain embodiments, system 601 is configured to adjust the flow rate of carbon dioxide to the cathode and/or the flow rate of anode feed material to the anode of reactor 603. Components that may be controlled for this purpose may include carbon oxide flow controller 613 and anode water controller 611.

Certain components of system 601 may operate to control the composition of the carbon dioxide feed stream and/or the anode feed stream. For example, water reservoir 621 and/or anode water additives source 623 may be controlled to adjust the composition of the anode feed stream. In some cases, additives source 623 may be configured to adjust the concentration of one or more solutes such as one or more salts in an aqueous anode feed stream.

In some cases, a temperature controller such controller 605 is configured to adjust the temperature of one or more components of system 601 based on a phase of operation. For example, the temperature of cell 603 may be increased or decreased during break-in, a current pause in normal operation, and/or storage.

In some embodiments, a carbon dioxide electrolytic reduction system is configured to facilitate removal of a reduction cell from other system components. This may be useful with the cell needs to be removed for storage, maintenance, refurbishment, etc. In the depicted embodiments, isolation valves 625a and 625b are configured to block fluidic communication of cell 603 to a source of carbon oxide to the cathode and backpressure controller 615, respectively. Additionally, isolation valves 625c and 625d are configured to block fluidic communication of the cell to anode water inlet and outlet, respectively.

The carbon dioxide reduction reactor 603 may also operate under the control of one or more electrical power sources and associated controllers. See, block 633. Electrical power source and controller 633 may be programmed or otherwise configured to control current supplied to and/or to control voltage applied to the electrodes in reduction reactor 603. Any of the current profiles described herein may be programmed into power source and controller 633.

In certain embodiments, electric power source and controller 633 performs some but not all the operations necessary to implement control profiles of the carbon dioxide reduction reactor 603. A system operator or other responsible individual may act in conjunction with electrical power source and controller 633 to fully define the schedules and/or profiles of current applied to reduction reactor 603.

In certain embodiments, electric power source and controller 633 controls operation of all or certain components of an upstream or downstream system. In certain embodiments, the electrical power source and controller acts in concert with one or more other controllers or control mechanisms associated with other components of system 601. For example, electrical power source and controller 633 may act in concert with controllers for controlling the purification of carbon oxide, the delivery of carbon oxide to the cathode, the delivery of anode water to the anode, the addition of pure water or additives to the anode water, delivery of carbon monoxide to a downstream system, and any combination of these features. In some implementations, one or more controllers are configured to control or operate in concert to control any combination of the following functions: applying current and/or voltage to reduction reactor 603, controlling backpressure (e.g., via backpressure controller 615), supplying purge gas (e.g., using purge gas component 617), delivering carbon dioxide (e.g., via carbon dioxide flow controller 613), humidifying carbon dioxide in a cathode feed stream (e.g., via humidifier 604), flow of anode water to and/or from the anode (e.g., via anode water flow controller 611), and anode water composition (e.g., via anode water source 605, pure water reservoir 621, and/or anode water additives component 623).

In the depicted embodiment, a voltage monitoring system 634 is employed to determine the voltage across an anode and cathode of an MEA cell or across any two electrodes of a cell stack, e.g., determining the voltage across all cells in a multi-cell stack. In certain embodiments, voltage monitoring system 634 is configured to work in concert with power supply 633 to cause reduction reactor 603 to remain within a specified voltage range. If, for example the cell's voltage deviates from a defined range (as determined by voltage monitoring system 634), power supply may be configured to apply current or voltage to the electrodes to maintain the cell voltage within the specified range.

An electrolytic carbon dioxide reduction system such as that depicted in FIG. 6 may employ a control system that includes one or more controllers and one or more controllable components such as pumps, sensors, dispensers, valves, and power supplies. Examples of sensors include pressure sensors, temperature sensors, flow sensors, conductivity sensors, voltmeters, ammeters, electrolyte composition sensors including electrochemical instrumentation, chromatography systems, optical sensors such as absorbance measuring tools, and the like. Such sensors may be coupled to inlets and/or outlets of an MEA cell (e.g., in a flow field), in a reservoir for holding anode water, pure water, salt solution, etc., and/or other components of an electrolytic carbon oxide reduction system.

Among the various functions that may be controlled by one or more controllers are: applying current and/or voltage to a carbon dioxide reduction cell, controlling backpressure on an outlet from a cathode on such cell, supplying purge gas to a cathode inlet, delivering carbon dioxide to the cathode inlet, humidifying carbon dioxide in a cathode feed stream, flowing anode water to and/or from the anode, and controller anode feed composition. Any one or more of these functions may have a dedicated controller for controlling its function alone. Any two or more of these functions may share a controller. In some embodiments, a hierarchy of controllers is employed, with at least one master controller providing instructions to two or more component controllers. For example, a system may comprise a master controller configured to provide high level control instructions to (i) a power supply to a carbon oxide reduction cell, (ii) a cathode feed stream flow controller, and (iii) an anode feed stream flow controller. For example, a programmable logic controller (PLC) may be used to control individual components of the system.

A controller may be integrated with electronics for controlling operation the electrolytic cell before, during, and after reducing a carbon oxide. The controller may control various components or subparts of one or multiple electrolytic carbon oxide reduction systems. The controller, depending on the processing requirements and/or the type of system, may be programmed to control any of the processes disclosed herein, such as delivery of gases, temperature settings (e.g., heating and/or cooling), pressure settings, power settings (e.g., electrical voltage and/or current delivered to electrodes of an MEA cell), liquid flow rate settings, fluid delivery settings, and dosing of purified water and/or salt solution. These controlled processes may be connected to or interfaced with one or more systems that work in concert with the electrolytic carbon oxide reduction system.

A controller may include any number of processors and/or memory devices. The controller may contain control logic such software or firmware and/or may execute instructions provided from another source. In various embodiments, a controller comprises electronics having various integrated circuits, logic, memory, and/or software that receive instructions, issue instructions, control operations described herein. The integrated circuits may include chips in the form of firmware that store program instructions, digital signal processors (DSPs), chips defined as application specific integrated circuits (ASICs), and/or one or more microprocessors, or microcontrollers that execute program instructions (e.g., software). Program instructions may be instructions communicated to the controller in the form of various individual settings (or program files), defining operational parameters for carrying out a process on one or more components of an electrolytic carbon oxide reduction system. The operational parameters may, in some embodiments, be part of a recipe defined by process engineers to accomplish one or more processing steps during generation of a particular reduction product such as carbon monoxide, hydrocarbons, and/or other organic compounds.

The controller, in some implementations, may be a part of or coupled to a computer that is integrated with, coupled to the system, otherwise networked to the system, or a combination thereof. For example, the controller may utilize instructions stored remotely (e.g., in the "cloud") and/or execute remotely. The computer may enable remote access to the system to monitor current progress of electrolysis operations, examine a history of past electrolysis operations, examine trends or performance metrics from a plurality of electrolysis operations, to change parameters of current processing, to set processing steps to follow a current processing, or to start a new process. In some examples, a remote computer (e.g., a server) can provide process recipes to a system over a network, which may include a local network or the internet. The remote computer may include a user interface that enables entry or programming of parameters and/or settings, which are then communicated to the system from the remote computer. In some examples, the controller receives instructions in the form of data, which specify parameters for each of the processing steps to be performed during one or more operations.

The controller may be distributed, such as by comprising one or more discrete controllers that are networked together and working towards a common purpose, such as applying current to an MEA cell and other process controls described herein. An example of a distributed control system for such purposes includes one or more processors on a system for electrolytically reducing a carbon oxide and one or more processors located remotely (such as at the platform level or as part of a remote computer) that combine to control a process.

Controllers and any of various associated computational elements including processors, memory, instructions, routines, models, or other components are sometimes described or claimed as "configured to" perform a task or tasks. In such contexts, the phrase "configured to" is used to denote structure by indicating that the component includes structure (e.g., stored instructions, circuitry, etc.) that performs a task or tasks during operation. As such, a controller and/or associated component can be said to be configured to perform the task even when the specified component is not necessarily currently operational (e.g., is not on).

Controllers and other components that are "configured to" perform an operation may be implemented as hardware—for example, circuits, memory storing program instructions executable to implement the operation, etc. Additionally, controllers and other components "configured to" perform an operation may be implemented as hardware that is manipulated by software and/or firmware (e.g., an FPGA or a general-purpose processor executing software) to operate in manner that is capable of performing the recited task(s). Additionally, "configured to" can refer to one or more memories or memory elements storing computer executable instructions for performing the recited task(s). Such memory elements may include memory on a computer chip having processing logic.

Non-computation elements such as reactors such electrolyzers, membrane assemblies, layers, and catalyst particles may also be "configured" to perform certain functions. In such contexts, the phrase "configured to" indicate that the referenced structure has one or more features that allow the function to be performed. Examples of such features include physical and/or chemical properties such as dimensions, composition, porosity, etc.

What is claimed is:

1. A method for producing acetic acid from carbon dioxide comprising:
   receiving carbon monoxide produced by reduction of carbon dioxide in one or more carbon dioxide reduction electrolyzers and hydrogen produced by a water electrolyzer;
   directing a first feed stream comprising carbon monoxide from the one or more carbon dioxide reduction electrolyzers and hydrogen from the water electrolyzer to a methanol synthesis reactor;
   synthesizing methanol in the methanol synthesis reactor;
   directing a second feed stream comprising methanol from the methanol synthesis reactor and carbon monoxide from the one or more carbon dioxide reduction electrolyzers to an acetic acid synthesis reactor; and
   synthesizing acetic acid in the acetic acid synthesis reactor.

2. The method of claim 1, further comprising circulating boiling water and saturated steam in a heat integration loop configured to receive heat produced by exothermic reactions in the methanol synthesis reactor and the acetic acid synthesis reactor and heat the first and second feed streams.

3. The method of claim 2, wherein the received heat converts boiling water to saturated steam and heating the first and second feed streams converts the saturated steam to boiling water.

4. The method of claim 2, wherein the heat integration loop comprises a first heat exchanger and further comprising heating the first feed stream comprising carbon monoxide and hydrogen to a first elevated temperature in the first heat exchanger.

5. The method of claim 4, wherein the heat integration loop comprises a second heat exchanger and further comprising heating the second feed stream comprising carbon monoxide and methanol to a second elevated temperature in the second heat exchanger.

6. The method of claim 5, further comprising heating the second feed stream comprising carbon monoxide and methanol from the second elevated temperature to an acetic acid synthesis reaction temperature.

7. The method of claim 2, further comprising maintaining the boiling water and saturated steam in the heat integration loop at constant temperature.

8. The method of claim 1, further comprising outputting a first output stream comprising methanol, carbon monoxide, and hydrogen from the methanol synthesis reactor, and optionally cooling the first output stream to a first reduced temperature.

9. The method of claim 8, further comprising recycling the hydrogen and carbon monoxide in the first output stream from the first output stream to the first feed stream.

10. The method of claim 1, further comprising outputting a second output stream comprising acetic acid, methanol, and carbon monoxide from the acetic acid synthesis reactor.

11. The method of claim 1, further comprising splitting an output of the one or more carbon dioxide reduction electrolyzers comprising carbon monoxide to a first carbon monoxide stream and a second carbon monoxide stream, inputting the first carbon monoxide stream to the methanol synthesis reactor, and inputting the second carbon monoxide stream to the acetic acid synthesis reactor.

12. The method of claim 1, further comprising separating acetic acid from methanol to produce an acetic acid product stream and recycling the methanol to the acetic acid synthesis reactor.

13. The method of claim 1, wherein an output of the methanol synthesis reactor comprises methanol, carbon monoxide, and hydrogen.

14. The method of claim 13, further comprising separating the methanol from the carbon monoxide and the hydrogen in a first condenser.

15. The method of claim 14, wherein a condensed output of the first condenser comprises methanol and water, the water is produced as a byproduct in the methanol synthesis reactor, and further comprising removing water from the methanol, wherein the water is produced as a byproduct in the methanol synthesis reactor.

16. The method of claim 14, further comprising recycling and optionally repressurizing the separated carbon monoxide and hydrogen.

17. The method of claim 1, wherein an output of the acetic acid synthesis reactor comprises acetic acid, methanol, and carbon monoxide, and further comprising separating the acetic acid and methanol from the carbon monoxide in a second condenser and recycling the separated carbon monoxide to the acetic acid synthesis reactor.

18. The method of claim 1, further comprising mixing carbon monoxide produced by the one or more carbon dioxide reduction electrolyzers and hydrogen produced by the water electrolyzer to form a methanol synthesis reactor feed stream.

19. The method of claim 18, further comprising compressing the methanol synthesis reactor feed stream to a first reaction pressure and mixing a compressed carbon monoxide and hydrogen recycle stream with the compressed methanol synthesis reactor feed stream to form the first feed stream.

20. The method of claim 1, wherein an operating pressure of the methanol synthesis reactor is at least twice that of an operating pressure of the acetic acid synthesis reactor.

* * * * *